(12) United States Patent
Hahn et al.

(10) Patent No.: US 8,530,421 B2
(45) Date of Patent: Sep. 10, 2013

(54) ISOLATED POLYPEPTIDES USED FOR TREATMENT OF INFLAMMATORY DISEASES AND INHIBITING CANCER METASTASIS

(75) Inventors: Jang-Hee Hahn, Chuncheon-si (KR); Kyoung-Jin Lee, Seoul (KR); Sun-Hee Lee, Wonju-si (KR); Hyun-Mi Ju, Wonju-si (KR)

(73) Assignee: Supadelixir Inc., Kangwon-Do (KR)

( * ) Notice: Subject to any disclaimer, the term of this patent is extended or adjusted under 35 U.S.C. 154(b) by 0 days.

(21) Appl. No.: 13/503,262

(22) PCT Filed: Aug. 24, 2010

(86) PCT No.: PCT/KR2010/005619
§ 371 (c)(1),
(2), (4) Date: May 31, 2012

(87) PCT Pub. No.: WO2011/049289
PCT Pub. Date: Apr. 28, 2011

(65) Prior Publication Data
US 2012/0245091 A1 Sep. 27, 2012

(30) Foreign Application Priority Data
Oct. 23, 2009 (KR) .................. 10-2009-0101003

(51) Int. Cl.
*A61K 38/00* (2006.01)
*A61K 39/00* (2006.01)
*C12P 21/02* (2006.01)
*C07K 16/46* (2006.01)
*C07K 14/00* (2006.01)
*C07K 5/00* (2006.01)
*C07K 7/00* (2006.01)

(52) U.S. Cl.
USPC ..... 514/12.2; 514/19.8; 424/134.1; 435/69.7; 530/324; 530/330

(58) Field of Classification Search
None
See application file for complete search history.

(56) References Cited

U.S. PATENT DOCUMENTS 5,541,087 A * 7/1996 Lo et al. .................. 435/69.7
2007/0154450 A1* 7/2007 Muller et al. .............. 424/85.1
2008/0213279 A1 9/2008 Muller et al.

FOREIGN PATENT DOCUMENTS

KR 10-2008-0002213 * 1/2008
KR 10-2009-0064826 A 6/2009

OTHER PUBLICATIONS

Zetter, B.R., "Adhesion molecules in tumor metastasis", Seminars in Cancer Biology, vol. 4. pp. 219-229, (1993).

Bailly, M. et al. "Regulation of Protrusion Shape and Adhesion to the Substratum during Chemotactic Responses of Mammalian Carcinoma Cells", Experimental Cell Research ,vol. 241, pp. 285-299. (1998).

Frisch, S.M., et al., "Control of Adhesion Dependent Cell Survival by Focal Adhesion Kinase", The Journal of Cell Biology, vol. 13, No. 3, pp. 793-799, (Aug. 1996).

Hannigan, G.E., et al., "Regulation of cell adhesion and anchorage-dependent growth by a new β1-integrin-linked protein kinase", Nature, vol. 379, pp. 91-96, (Jan. 4, 1996).

Suh, J.S. "Control of Invasiveness of Human Breast Carcinoma Cell Line MCF-7 by CD99 Molecute", Kang won National University, 4 pages, Feb. 2002.

Byun, Hee-Jung, et al. "A Splice Variant of CD99 Increases Motility and MMP-9 Expression of Human Breast Cancer Cells through the AKT-, ERK-, and JNK- dependent AP-1 Activation Signaling Pathways", The Journal of Biological Chemistry, vol. 281, No. 46, pp. 34833-34847, ( Nov. 17, 2006).

Fouchet, C. et al., "A study of the coregulation and tissue specificity of XG and MIC2 gene expression in eukaryotic cells", Blood, vol. 95, No. 5, pp. 1819-1826, (Mar. 1, 2000).

Suh, Y.H., et al., "Cloning, genomic organization, alternative trancripts, and expresssion analysis of CD99L2, a novel paralog of human CD99, and identification of evolutionary conserved motifs", Gene, vol. 307, pp. 63-76, (2003).

Park, S.H., et al. "Rapid divergency of rodent CD99 orthologs: Implications for the evolution of the pseudoautosomal region", Gene, vol. 353, pp. 177-188, (2005).

Suh.J.S., "CD99 activation atenuates the adheion of MCF-7 cells to laminin, fibronectin, and collagen IV by reducing β1 inegrin activity", Kangwon National University, 2 pages, Feb. 2009.

Hsu, et al., "LPS-Induced TLR4 Signaling in Human Colorectal Cancer Cells Increases β1 Integrin-Mediated Cell Adhesion and Liver Metastasis", Cancer Res, vol. 71, pp. 1989-1998, (May 2011).

Takatsuki, et al., "Adhesion of Gastric Carcinoma Cells to Peritoneum Mediated by α3β1 Integrin (VLA-3)", Cancer Res, vol. 64, pp. 6065-6070, (Sep. 2004).

(Continued)

*Primary Examiner* — Elly-Gerald Stoica
(74) *Attorney, Agent, or Firm* — Vorys, Sater, Seymour & Pease LLP; Mih Suhn Koh

(57) ABSTRACT

The present invention relates to a polypeptide derived from a highly conserved region (HCR) I-III of an extracellular region of a CD99 and CD99 family such as CD99L2 and PBDX(or XG), which are a kind of transmembrane protein, or a fused protein thereof. The polypeptide or the fused protein thereof has an activating function of inhibiting the extravasation of white blood cells, or inhibiting the growth and/or metastasis of cancer cells. The present invention also provides a polynucleotide coding the polypeptide, a vector including same, and a transformant transformed by the vector. In addition, the present invention provides a pharmaceutical composition including the polypeptide or the fused protein thereof for preventing or treating inflammatory diseases. Further, the present invention provides a is pharmaceutical composition including the polypeptide or the fused protein thereof inhibiting the growth and/or metastasis of cancer cells, i.e., a pharmaceutical composition for preventing or treating cancer.

14 Claims, 13 Drawing Sheets

(56) References Cited

OTHER PUBLICATIONS

Kato, et al., "The Primary of β1 Integrin Activation in the Metastatic Cascade", PLoS ONE, vol. 7, Issue 10, p. e46576 (11 pages), (Oct. 2012).

Trerotola, et al., "Trop-2 Promotes Prostate Cancer Metastasis by Modulating β1 Integrin Functions", Cancer Res, vol. 73, pp. 3155-3167, (Mar. 2013).

Tringali, et al., "The Plasma Membrane Sialidase NEU3 Regulates the Malignancy of Renal Carcinoma Cells by Controlling β1 Integrin Internalization and Recycling", The Journal of Biological Chemistry, vol. 287, No. 51, pp. 42835-42845, (Dec. 2012).

Barkan, et al., "β1-Integrin: A Potential Therapeutic Target in the Battle against Cancer Recurrence", Clin Cancer Res, vol. 17, pp. 7219-7223, (Sep. 2011).

Yang, et al., "Integrin α1β1 and α2β1 Are the Key Regulators of Hepatocarcinoma Cell Invasion Across the Fibrotic Matrix Microenvironment", Cancer Res, vol. 63, pp. 8312-8317, (Dec. 2003).

Wang, et al., "The Pivotal Role of Integrin β1 in Metastasis of Head and Neck Squamous Cell Carcinoma", Clin Cancer Res, vol. 18, pp. 4589-4599, (Jul. 2012).

Chen, et al., "A Novel Sialyltransferase Inhibitor Suppresses FAK/Paxillin Signaling and Cancer Angiogenesis and Metastasis Pathways", Cancer Res, vol. 71, pp. 473-483, (Jan. 2011).

* cited by examiner

Time after challenge

```
SEQUENCE LISTING

<160> NUMBER OF SEQ ID NOS: 35

<210> SEQ ID NO 1
<211> LENGTH: 185
<212> TYPE: PRT
<213> ORGANISM: Homo sapiens

<400> SEQUENCE: 1

Met Ala Arg Gly Ala Ala Leu Ala Leu Leu Leu Phe Gly Leu Leu Gly
 1               5                  10                  15

Val Leu Val Ala Ala Pro Asp Gly Gly Phe Asp Leu Ser Asp Ala Leu
            20                  25                  30

Pro Asp Asn Glu Asn Lys Lys Pro Thr Ala Ile Pro Lys Lys Pro Ser
        35                  40                  45

Ala Gly Asp Asp Phe Asp Leu Gly Asp Ala Val Val Asp Gly Glu Asn
    50                  55                  60

Asp Asp Pro Arg Pro Pro Asn Pro Lys Pro Met Pro Asn Pro Asn
65                  70                  75                  80

Pro Asn His Pro Ser Ser Ser Gly Ser Phe Ser Asp Ala Asp Leu Ala
                85                  90                  95

Asp Gly Val Ser Gly Gly Glu Gly Lys Gly Gly Ser Asp Gly Gly Gly
            100                 105                 110
```

Ser His Arg Lys Glu Gly Glu Ala Asp Ala Pro Gly Val Ile Pro
            115                 120                 125

Gly Ile Val Gly Ala Val Val Ala Val Ala Gly Ala Ile Ser Ser
        130                 135                 140

Phe Ile Ala Tyr Gln Lys Lys Leu Cys Phe Lys Glu Asn Ala Glu
145                 150                 155                 160

Gln Gly Glu Val Asp Met Glu Ser His Arg Asn Ala Asn Ala Glu Pro
                165                 170                 175

Ala Val Gln Arg Thr Leu Leu Glu Lys
            180                 185

<210> SEQ ID NO 2
<211> LENGTH: 262
<212> TYPE: PRT
<213> ORGANISM: Homo sapiens

<400> SEQUENCE: 2

Met Val Ala Trp Arg Ser Ala Phe Leu Val Cys Leu Ala Phe Ser Leu
  1               5                  10                  15

Ala Thr Leu Val Gln Arg Gly Ser Gly Asp Phe Asp Asp Phe Asn Leu
                 20                  25                  30

Glu Asp Ala Val Lys Glu Thr Ser Ser Val Lys Gln Pro Trp Asp His
             35                  40                  45

Thr Thr Thr Thr Thr Thr Asn Arg Pro Gly Thr Thr Arg Ala Pro Ala
         50                  55                  60

Lys Pro Pro Gly Ser Gly Leu Asp Leu Ala Asp Ala Leu Asp Asp Gln
 65                  70                  75                  80

Asp Asp Gly Arg Arg Lys Pro Gly Ile Gly Gly Arg Glu Arg Trp Asn
                 85                  90                  95

His Val Thr Thr Thr Thr Lys Arg Pro Val Thr Thr Arg Ala Pro Ala
            100                 105                 110

Asn Thr Leu Gly Asn Asp Phe Asp Leu Ala Asp Ala Leu Asp Asp Arg
        115                 120                 125

Asn Asp Arg Asp Asp Gly Arg Arg Lys Pro Ile Ala Gly Gly Gly Gly
    130                 135                 140

Phe Ser Asp Lys Asp Leu Glu Asp Ile Val Gly Gly Gly Glu Tyr Lys
145                 150                 155                 160

Pro Asp Lys Gly Lys Gly Asp Gly Arg Tyr Gly Ser Asn Asp Asp Pro
                165                 170                 175

Gly Ser Gly Met Val Ala Glu Pro Gly Thr Ile Ala Gly Val Ala Ser
            180                 185                 190

Ala Leu Ala Met Ala Leu Ile Gly Ala Val Ser Ser Tyr Ile Ser Tyr
        195                 200                 205

Gln Gln Lys Lys Phe Cys Phe Ser Ile Gln Gln Gly Leu Asn Ala Asp
    210                 215                 220

Tyr Val Lys Gly Glu Asn Leu Glu Ala Val Val Cys Glu Glu Pro Gln
225                 230                 235                 240

Val Lys Tyr Ser Thr Leu His Thr Gln Ser Ala Glu Pro Pro Pro Pro
                245                 250                 255

Pro Glu Pro Ala Arg Ile
            260

<210> SEQ ID NO 3
<211> LENGTH: 180
<212> TYPE: PRT
<213> ORGANISM: Homo sapiens

<400> SEQUENCE: 3

```
Met Glu Ser Trp Trp Gly Leu Pro Cys Leu Ala Phe Leu Cys Phe Leu
  1               5                  10                  15
Met His Ala Arg Gly Gln Arg Asp Phe Asp Leu Ala Asp Ala Leu Asp
                 20                  25                  30
Asp Pro Glu Pro Thr Lys Lys Pro Asn Ser Asp Ile Tyr Pro Lys Pro
             35                  40                  45
Lys Pro Pro Tyr Tyr Pro Gln Pro Glu Asn Pro Asp Ser Gly Gly Asn
         50                  55                  60
Ile Tyr Pro Arg Pro Lys Pro Arg Pro Gln Pro Gln Pro Gly Asn Ser
 65                  70                  75                  80
Gly Asn Ser Gly Gly Tyr Phe Asn Asp Val Asp Arg Asp Asp Gly Arg
                 85                  90                  95
Tyr Pro Pro Arg Pro Arg Pro Arg Pro Ala Gly Gly Gly Gly Gly Gly
            100                 105                 110
Gly Tyr Ser Ser Tyr Gly Asn Ser Asp Asn Thr His Gly Gly Asp His
            115                 120                 125
His Ser Thr Tyr Gly Asn Pro Glu Gly Asn Met Val Ala Lys Ile Val
            130                 135                 140
Ser Pro Ile Val Ser Val Val Val Thr Leu Leu Gly Ala Ala Ala
145                 150                 155                 160
Ser Tyr Phe Lys Leu Asn Asn Arg Arg Asn Cys Phe Arg Thr His Glu
                165                 170                 175
Pro Glu Asn Val
            180
```

<210> SEQ ID NO 4
<211> LENGTH: 159
<212> TYPE: PRT
<213> ORGANISM: Homo sapiens

<400> SEQUENCE: 4

```
Asp Phe Asp Asp Phe Asn Leu Glu Asp Ala Val Lys Glu Thr Ser Ser
  1               5                  10                  15
Val Lys Gln Pro Trp Asp His Thr Thr Thr Thr Thr Asn Arg Pro
                 20                  25                  30
Gly Thr Thr Arg Ala Pro Ala Lys Pro Pro Gly Ser Gly Leu Asp Leu
             35                  40                  45
Ala Asp Ala Leu Asp Asp Gln Asp Asp Gly Arg Arg Lys Pro Gly Ile
         50                  55                  60
Gly Gly Arg Glu Arg Trp Asn His Val Thr Thr Thr Lys Arg Pro
 65                  70                  75                  80
Val Thr Thr Arg Ala Pro Ala Asn Thr Leu Gly Asn Asp Phe Asp Leu
                 85                  90                  95
Ala Asp Ala Leu Asp Asp Arg Asn Asp Arg Asp Gly Arg Arg Lys
            100                 105                 110
Pro Ile Ala Gly Gly Gly Phe Ser Asp Lys Asp Leu Glu Asp Ile
            115                 120                 125
Val Gly Gly Gly Glu Tyr Lys Pro Asp Lys Lys Gly Asp Gly Arg
            130                 135                 140
Tyr Gly Ser Asn Asp Asp Pro Gly Ser Gly Met Val Ala Glu Pro
145                 150                 155
```

<210> SEQ ID NO 5
<211> LENGTH: 119

```
<212> TYPE: PRT
<213> ORGANISM: Homo sapiens

<400> SEQUENCE: 5

His Ala Arg Gly Gln Arg Asp Phe Asp Leu Ala Asp Ala Leu Asp Asp
 1               5                  10                  15

Pro Glu Pro Thr Lys Lys Pro Asn Ser Asp Ile Tyr Pro Lys Pro Lys
                20                  25                  30

Pro Pro Tyr Tyr Pro Gln Pro Glu Asn Pro Asp Ser Gly Gly Asn Ile
            35                  40                  45

Tyr Pro Arg Pro Lys Pro Arg Pro Gln Pro Gln Pro Gly Asn Ser Gly
    50                  55                  60

Asn Ser Gly Gly Tyr Phe Asn Asp Val Asp Arg Asp Asp Gly Arg Tyr
 65                  70                  75                  80

Pro Pro Arg Pro Arg Pro Arg Pro Ala Gly Gly Gly Gly Gly
                85                  90                  95

Tyr Ser Ser Tyr Gly Asn Ser Asn Thr His Gly Gly Asp His His
            100                 105                 110

Ser Thr Tyr Gly Asn Pro Glu
        115

<210> SEQ ID NO 6
<211> LENGTH: 7
<212> TYPE: PRT
<213> ORGANISM: Homo sapiens

<400> SEQUENCE: 6

Phe Asp Leu Ser Asp Ala Leu
 1               5

<210> SEQ ID NO 7
<211> LENGTH: 7
<212> TYPE: PRT
<213> ORGANISM: Homo sapiens

<400> SEQUENCE: 7

Phe Asp Leu Gly Asp Ala Val
 1               5

<210> SEQ ID NO 8
<211> LENGTH: 7
<212> TYPE: PRT
<213> ORGANISM: Homo sapiens

<400> SEQUENCE: 8

Phe Asn Leu Glu Asp Ala Val
 1               5

<210> SEQ ID NO 9
<211> LENGTH: 7
<212> TYPE: PRT
<213> ORGANISM: Homo sapiens

<400> SEQUENCE: 9

Phe Asp Leu Ala Asp Ala Leu
 1               5

<210> SEQ ID NO 10
<211> LENGTH: 8
<212> TYPE: PRT
<213> ORGANISM: Homo sapiens

<400> SEQUENCE: 10
```

```
Phe Ser Asp Lys Asp Leu Glu Asp
  1               5
```

<210> SEQ ID NO 11
<211> LENGTH: 3
<212> TYPE: PRT
<213> ORGANISM: Homo sapiens

<400> SEQUENCE: 11

```
Leu Ser Asp
  1
```

<210> SEQ ID NO 12
<211> LENGTH: 3
<212> TYPE: PRT
<213> ORGANISM: Homo sapiens

<400> SEQUENCE: 12

```
Leu Gly Asp
  1
```

<210> SEQ ID NO 13
<211> LENGTH: 3
<212> TYPE: PRT
<213> ORGANISM: Homo sapiens

<400> SEQUENCE: 13

```
Leu Ala Asp
  1
```

<210> SEQ ID NO 14
<211> LENGTH: 3
<212> TYPE: PRT
<213> ORGANISM: Homo sapiens

<400> SEQUENCE: 14

```
Leu Glu Asp
  1
```

<210> SEQ ID NO 15
<211> LENGTH: 6
<212> TYPE: PRT
<213> ORGANISM: Artificial Sequence
<220> FEATURE:
<223> OTHER INFORMATION: poly-His fragment

<400> SEQUENCE: 15

```
His His His His His His
  1               5
```

<210> SEQ ID NO 16
<211> LENGTH: 330
<212> TYPE: PRT
<213> ORGANISM: Artificial Sequence
<220> FEATURE:
<223> OTHER INFORMATION: Fc fragment

<400> SEQUENCE: 16

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45
```

```
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 17
<211> LENGTH: 561
<212> TYPE: DNA
<213> ORGANISM: Homo sapiens

<400> SEQUENCE: 17
atggccatgg cccgcggggc tgcgctggcg ctgctgctct tcggcctgct gggtgttctg      60
gtcgccgccc cggatggtgg tttcgattta tccgatgccc ttcctgacaa tgaaaacaag     120
aaacccactg caatccccaa gaaacccagt gctggggatg actttgactt aggagatgct     180
gttgttgatg agaaaatga cgacccacga ccaccgaacc cacccaaacc gatgccaaat     240
ccaaacccca accaccctag ttcctccggt agcttttcag atgctgacct tgcggatggc     300
gtttcaggtg agaaggaaa aggaggcagt gatggtggag cagccacag aaagaaggg       360 gaagaggccg acgcccagg cgtgatcccc gggattgtgg gggctgtcgt ggtcgccgtg     420
gctggagcca tctctagctt cattgcttac cagaaaaaga agctatgctt caaagaaaat     480
gcagaacaag gggaggtgga catggagagc accggaatg ccaacgcaga gccagctgtt     540
```

```
cagcgtactc ttttagagaa a                                            561
```

<210> SEQ ID NO 18
<211> LENGTH: 786
<212> TYPE: DNA
<213> ORGANISM: Homo sapiens

<400> SEQUENCE: 18

```
atggtggcct ggcgctcggc gttccttgtc tgcctcgctt tctccttggc caccctggtc    60
cagcgaggat ctggggactt tgatgatttt aacctggagg atgcagtgaa agaaacttcc   120
tcagtaaagc agccatggga ccacaccacc accaccacaa ccaataggcc aggaaccacc   180
agagctccgg caaaacctcc aggtagtgga ttggacttgg ctgatgcttt ggatgatcaa   240
gatgatggcc gcaggaaacc gggtatagga ggaagagaga gatggaacca tgtaaccacc   300
acgaccaaga ggccagtaac caccagagct ccagcaaata ctttaggaaa tgattttgac   360
ttggctgatg ccctggatga tcgaaatgat cgagatgatg ccgcaggaa  accaattgct   420
ggaggaggag gttttttcaga caaggatctt gaagacatag taggggggtgg agaatacaaa   480
cctgacaagg gtaaaggtga tggccggtac ggcagcaatg acgaccctgg atctggcatg   540
gtggcagagc ctggcaccat tgccggggtg gccagcgccc tggccatggc cctcatcggt   600
gccgtctcca gctacatctc ctaccagcag aagaagttct gcttcagcat tcagcagggt   660
ctcaacgcag actacgtgaa gggagagaac ctggaagccg tggtatgtga ggaaccccaa   720
gtgaaatact ccacgttgca cacgcagtct gcagagccgc cgccgccgcc cgaaccagcc   780
cggatc                                                              786
```

<210> SEQ ID NO 19
<211> LENGTH: 540
<212> TYPE: DNA
<213> ORGANISM: Homo sapiens

<400> SEQUENCE: 19

```
atggagagct ggtggggact tccctgtctt gcgttcctgt gttttctaat gcacgcccga    60
ggtcaaagag actttgattt ggcagatgcc cttgatgacc ctgaacccac caagaagcca   120
aactcagata tctacccaaa gccaaaacca ccttactacc cacagcccga gaatcccgac   180
agcggtggaa atatctaccc aaggccaaag ccacgccctc aacccagcc  tggcaattcc   240
ggcaacagtg gaggttactt caatgatgtg gaccgtgatg acggacgcta cccgcccagg   300
cccaggccac ggccgcctgc aggaggtggc ggcggtggct actccagtta tggcaactcc   360
gacaacacgc acggtggaga tcaccattca acgtatggca atccagaagg caatatggta   420
gcaaaaatcg tgtctcccat cgtatccgtg tggtggtgga cactgctggg agcagcagcc   480
agttatttca aactaaacaa taggagaaat tgtttcagga cccatgaacc agaaaatgtc   540
```

<210> SEQ ID NO 20
<211> LENGTH: 477
<212> TYPE: DNA
<213> ORGANISM: Homo sapiens

<400> SEQUENCE: 20

```
gactttgatg attttaacct ggaggatgca gtgaaagaaa cttcctcagt aaagcagcca    60
tgggaccaca ccaccaccac cacaaccaat aggccaggaa ccaccagagc tccggcaaaa   120
cctccaggta gtggattgga cttggctgat gctttggatg atcaagatga tggccgcagg   180
aaaccgggta taggaggaag agagagatgg aaccatgtaa ccaccacgac caagaggcca   240
```

```
gtaaccacca gagctccagc aaatacttta ggaaatgatt ttgacttggc tgatgccctg    300
gatgatcgaa atgatcgaga tgatggccgc aggaaaccaa ttgctggagg aggaggtttt    360
tcagacaagg atcttgaaga catagtaggg ggtggagaat acaaacctga caagggtaaa    420
ggtgatggcc ggtacggcag caatgacgac cctggatctg catggtggc agagcct        477
```

<210> SEQ ID NO 21
<211> LENGTH: 357
<212> TYPE: DNA
<213> ORGANISM: Homo sapiens

<400> SEQUENCE: 21

```
cacgcccgag gtcaaagaga cttttgatttg gcagatgccc ttgatgaccc tgaacccacc    60
aagaagccaa actcagatat ctacccaaag ccaaaaccac cttactaccc acagcccgag   120
aatcccgaca gcggtggaaa tatctaccca aggccaaagc cacgccctca accccagcct   180
ggcaattccg gcaacagtgg aggttacttc aatgatgtgg accgtgatga cggacgctac   240
ccgcccaggc ccaggccacg gccgcctgca ggaggtggcg gcggtggcta ctccagttat   300
ggcaactccg acaacacgca cggtggagat caccattcaa cgtatggcaa tccagaa      357
```

<210> SEQ ID NO 22
<211> LENGTH: 21
<212> TYPE: DNA
<213> ORGANISM: Homo sapiens

<400> SEQUENCE: 22

```
ttcgatttat ccgatgccct t                                               21
```

<210> SEQ ID NO 23
<211> LENGTH: 21
<212> TYPE: DNA
<213> ORGANISM: Homo sapiens

<400> SEQUENCE: 23

```
tttgacttag gagatgctgt t                                               21
```

<210> SEQ ID NO 24
<211> LENGTH: 21
<212> TYPE: DNA
<213> ORGANISM: Homo sapiens

<400> SEQUENCE: 24

```
tttaacctgg aggatgcagt g                                               21
```

<210> SEQ ID NO 25
<211> LENGTH: 21
<212> TYPE: DNA
<213> ORGANISM: Homo sapiens

<400> SEQUENCE: 25

```
tttgacttgg ctgatgccct g                                               21
```

<210> SEQ ID NO 26
<211> LENGTH: 21
<212> TYPE: DNA
<213> ORGANISM: Homo sapiens

<400> SEQUENCE: 26

```
tttgatttgg cagatgccct t                                               21
```

<210> SEQ ID NO 27

```
<211> LENGTH: 24
<212> TYPE: DNA
<213> ORGANISM: Homo sapiens

<400> SEQUENCE: 27
ttttcagaca aggatcttga agac                                              24

<210> SEQ ID NO 28
<211> LENGTH: 9
<212> TYPE: DNA
<213> ORGANISM: Homo sapiens

<400> SEQUENCE: 28 ttatccgat                                                                9

<210> SEQ ID NO 29
<211> LENGTH: 9
<212> TYPE: DNA
<213> ORGANISM: Homo sapiens

<400> SEQUENCE: 29 ttaggagat                                                                9

<210> SEQ ID NO 30
<211> LENGTH: 9
<212> TYPE: DNA
<213> ORGANISM: Homo sapiens

<400> SEQUENCE: 30 ttggctgat                                                                9

<210> SEQ ID NO 31
<211> LENGTH: 9
<212> TYPE: DNA
<213> ORGANISM: Homo sapiens

<400> SEQUENCE: 31 ttggcagat                                                                9

<210> SEQ ID NO 32
<211> LENGTH: 9
<212> TYPE: DNA
<213> ORGANISM: Homo sapiens

<400> SEQUENCE: 32 ctggaggat                                                                9

<210> SEQ ID NO 33
<211> LENGTH: 9
<212> TYPE: DNA
<213> ORGANISM: Homo sapiens

<400> SEQUENCE: 33 cttgaagac                                                                9

<210> SEQ ID NO 34
<211> LENGTH: 18
<212> TYPE: DNA
<213> ORGANISM: Artificial Sequence
<220> FEATURE:
<223> OTHER INFORMATION: poly-His fragment sequence

<400> SEQUENCE: 34
caccaccacc accaccat                                                     18
```

```
<210> SEQ ID NO 35
<211> LENGTH: 993
<212> TYPE: DNA
<213> ORGANISM: Artificial Sequence
<220> FEATURE:
<223> OTHER INFORMATION: Fc fragment sequence

<400> SEQUENCE: 35
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa tga                                  993
```

ISOLATED POLYPEPTIDES USED FOR TREATMENT OF INFLAMMATORY DISEASES AND INHIBITING CANCER METASTASIS

This is a National Phase Application filed under 35 U.S.C. 371 as a national stage of PCT/KR2010/005619, filed Aug. 24, 2010, and claiming the benefit from Korean Application No. 10-2009-0101003, filed Oct. 23, 2009, the content of each of which is hereby incorporated by reference in its entirety.

The Sequence Listing submitted in text format (.txt) on May 30, 2012, named "Sequence_Listing_Corrected.txt", (created on Wednesday, May 30, 2012, 19.2 KB), is incorporated herein by reference.

TECHNICAL FIELD

The present invention relates to a polypeptide or its fusion protein having an inhibitory activity against transmigration of leukocytes or an inhibitory activity against growth and/or metastasis of cancer cells, the polypeptide being derived from highly conserved region (HCR) I-III in the external domain of CD99 and its family, i.e., CD99, CD99L2, and PBDX (or XG). The present invention also relates to a polynucleotide encoding the polypeptide, a vector including the polynucleotide, and a transformant transformed with the vector. The present invention also relates to a pharmaceutical composition for the prevention or treatment of inflammatory diseases including the polypeptide or its fusion protein. The present invention also relates to a pharmaceutical composition for inhibiting the growth and/or metastasis of cancer cells including the polypeptide or its fusion protein.

BACKGROUND ART

An inflammatory response is known as a protective response of living organism for rehabilitating the structures and functions of tissues damaged by infection, trauma, etc. Mobilization of leukocytes to a focus of inflammation is critical for the rapid resolution of infections and restoration of tissue damages resulting from a variety of injuries. However, a misdirected or prolonged inflammatory response causes damage to the body's tissues or diseases. For example, inflammatory diseases are caused by bacterial or viral infection, e.g., cerebrospinal meningitis, enteritis, dermatitis, uveitis, encephalitis, or adult respiratory distress syndrome, or non-infectious factors, e.g., trauma, autoimmune diseases, or organ transplantation rejection. Inflammatory diseases are classified into acute and chronic inflammatory diseases according to symptoms or pathological features. Acute inflammation such as allergy or bacterial/viral infection is manifested as local signs such as a change in bloodstream, blood vessel size, and vascular permeability, and the recruitment of leukocytes. In contrast, a main pathological feature of chronic inflammation such as rheumatoid arthritis, arthero-sclerosis, chronic kidney infection, or hepatocirrhosis is a continuous emigration of macrophages, lymphocytes, or plasma cells into foci of inflammation due to recurrence of inflammatory factors, thereby causing a long-lasting inflammatory response.

In order to induce an inflammatory response, the emigration of leukocytes into inflammation foci is an essential event. Many cell adhesion molecules are implicated in the emigration of leukocytes. That is, the emigration of leukocytes includes a rolling stage in which leukocytes are mobilized to the blood vessels of inflamed sites by chemokine secreted from the inflamed sites and then rolled on surfaces of vascular endothelial cells while reducing the velocity of cell movement; an adhesion stage in which the leukocytes stops rolling and are firmly adhered to the vascular endothelial cells; and a transmigration stage wherein the leukocytes migrate through capillary vessels and basement membranes. The final stage, i.e., the transmigration stage is also called "diapedesis" or "transendothelial migration".

Cancer cells induced by carcinogens proliferate rapidly relative to normal cells, thereby forming tumor masses, invading surrounding tissues, and interfering with normal body functions. Cancer cells bring nutrients and oxygen by inducing angiogenesis, and metastasis thereof is also caused by angiogenesis. Although cancer cells grow infinitely at specific sites, they can also leave the sites from which they originated, migrate to and grow in new sites, whose process is called "metastasis". Metastasis involve several key steps: conversion of cancer cells to migratory mesenchymal cells, dissociation of the mesenchymal cells from the original tumor sites, invasion into and spread through surrounding connective tissues and capillary vessels, migration through blood vessels, escape from the blood vessels, migration through connective tissues, and proliferation in secondary sites.

Expression and activation of cell adhesion molecules on surfaces of tumor cells play a very important role in tumor metastasis (Zetter, B. R. (1993). Adhesion molecules in tumor metastasis. Semin Cancer Biol. 4: 219). Tumor metastasis is induced by regulating the expression pattern and activity of cell adhesion molecules on surfaces of tumor cells. In order to understand the metastasis of tumor cells, it is prerequisite to understand cell adhesion molecules and substances for regulating the expression and functions of the cell adhesion molecules (Bailly, M., Yan, L., Whitesides, G. M., Condeelis, J. S., and Segall, J. E. (1998). Regulation of protusion shape and adhesion to the sustratum during chemoacic responses of mammalian carcinoma cells. Exp Cell Res. 241: 285; Frisch, S. M., Vuori, K., Ruoslahti, E., and Chan-Hui., P. (1996). Control of adhesion-dependent cell survival by focal adhesion kinase. J Cell Biol 134: 793; and Hannigan, G. E., Leung-Hagesteijn, C., Fitz-Gibbon, L., Coppolino, M. G., Radeva, G., Filmus, J., Bell, J. C., and Dedhar, S. (1996). Regulation of cell adhesion and anchorage-dependent growth by a new β1-integrin-linked protein kinase. Nature 379: 91).

The present inventors have disclosed that when CD99 is activated, the function of $\beta_1$ integrin is altered, thereby preventing the adhesion of cancer cells onto extracellular matrices (ECMs). This suggests that CD99 may be involved in metastasis of cancer cells (Suh J S., 2001. Control of invasiveness of human breast carcinoma cell line MCF-7 by CD99 molecule. Kangwon National University). In addition, the present inventors have disclosed that a polypeptide derived from CD99, i.e., a polypeptide comprising the peptide from position 94 to position 97 of CD99, can effectively activate CD99, thereby inhibiting the transmigration of leukocytes or the growth and/or metastasis of cancer cells (International Patent Publication No: WO 2007/037601).

Meanwhile, CD99 forms a CD99 family along with CD99L2 and PBDX (or XG) (Fouchet C, Gane P, Huet M, Fellous M, Rouger P, Banting G, Cartron J P, Lopez C. 2000. A study of the coregulation and tissue specificity of XG and MIC2 gene expression in eukaryotic cells. *Blood* 95:1819; Suh Y H, Shin Y K, Kook M C, Oh K I, Park W S, Kim S H, Lee I S, Park H J, Huh T L, Park S H. 2003. Cloning, genomic organization, alternative transcripts and expression analysis of CD99L2, a novel paralog of human CD99, and identification of evolutionary conserved motifs. *Gene* 307:63; Park S H, Shin Y K, Suh Y H, Park W S, Ban Y L, Choi H S, Park H J, Jung KC. 2005. Rapid divergency of rodent CD99 orthologs: implications for the evolution of the pseudoautosomal region. *Gene* 353(2):177). The CD99 family is one of the type 1 transmembrane proteins, consisting of a glycosylated external domain, a transmembrane domain, and an internal domain. The HCR I-III in CD99 and CD99L2 are located in the external domain thereof, and play a key role in binding between CD99 proteins and in inactivating $\beta_1$ integrin (Suh J S., 2009. CD99 activation attenuates the adhesion of MCF-7 cells to laminin, fibronectin, and collagen IV by reducing $\beta_1$ integrin activity. Kangwon National University). HCR II is also located in PBDX(or XG).

DETAILED DESCRIPTION OF THE INVENTION

Technical Problem

The present inventors have found that a polypeptide or its fusion protein having a certain amino acid sequence derived from highly conserved regions (HCRs) of CD99 and its family, i.e., CD99, CD99L2, and PBDX(or XG) can inhibit the transmigration of leukocytes, thereby inhibiting inflammatory reaction; and also can inhibit angiogenesis and the trans-endothelial migration of cancer cells, thereby inhibiting the growth and/or metastasis of cancer cells.

Therefore, the present invention provides a polypeptide or its fusion protein having an inhibitory activity against transmigration of leukocytes or an inhibitory activity against growth and/or metastasis of cancer cells, the polypeptide being derived from the HCRs of CD99, CD99L2, and PBDX (or XG).

The present invention also provides a polynucleotide encoding the polypeptide and a vector including the polynucleotide.

The present invention also provides a transformant obtained by transforming a host cell with the vector.

The present invention also provides a pharmaceutical composition for the prevention or treatment of inflammatory diseases, including the polypeptide or its fusion protein as an active ingredient and a pharmaceutically acceptable carrier.

The present invention also provides a pharmaceutical composition for inhibiting the growth and/or metastasis of cancer cells (i.e., for preventing or treating a cancer), including the polypeptide or its fusion protein as an active ingredient and a pharmaceutically acceptable carrier.

TECHNICAL SOLUTION

In accordance with an aspect of the present invention, there is provided a polypeptide having an inhibitory activity against transmigration of leukocytes or an inhibitory activity against growth and/or metastasis of cancer cells, wherein the polypeptide is selected from the group consisting of a polypeptide consisting of 3 to 96 amino acids derived from the polypeptide of SEQ ID NO: 1, said polypeptide comprising the peptide from position 28 to position 30 or from position 55 to position 57 of SEQ ID NO: 1, with the proviso that a polypeptide comprising the peptide from position 94 to position 97 of SEQ ID NO: 1 is excluded; a polypeptide consisting of 3 to 200 amino acids derived from the polypeptide of SEQ ID NO: 2, said polypeptide comprising the peptide from position 32 to position 34, from position 73 to position 75, from position 121 to position 123, or from position 150 to position 152 of SEQ ID NO: 2; and a polypeptide consisting of 3 to 130 amino acids derived from the polypeptide of SEQ ID NO: 3, said polypeptide comprising the peptide from position 27 to position 29 of SEQ ID NO: 3.

In accordance with another aspect of the present invention, there is provided a fusion protein of the polypeptide and a polyhistidine (poly-His) region or a fusion protein of the polypeptide and a Fc region.

In accordance with still another aspect of the present invention, there is provided a polynucleotide encoding the polypeptide.

In accordance with still another aspect of the present invention, there is provided a vector comprising the polynucleotide encoding the polypeptide.

In accordance with still another aspect of the present invention, there is provided a transformant obtained by transforming a host cell with the vector.

In accordance with yet another aspect of the present invention, there is provided a pharmaceutical composition for the prevention or treatment of inflammatory diseases, comprising the polypeptide or its fusion protein as an active ingredient and a pharmaceutically acceptable carrier.

In accordance with a further aspect of the present invention, there is provided a pharmaceutical composition for inhibiting the growth and/or metastasis of cancer cells, comprising the polypeptide or its fusion protein as an active ingredient and a pharmaceutically acceptable carrier.

Advantageous Effects

The polypeptide or its fusion protein according to the present invention can inhibit the transmigration of leukocytes, thereby applying to a pharmaceutical composition for inhibiting inflammation. And also, the polypeptide or its fusion protein according to the present invention can inhibit angiogenesis and trans-endothelial migration of cancer cells, thereby inhibiting the growth and/or metastasis of cancer cells. Therefore, the polypeptide or its fusion protein can be usefully applied to a pharmaceutical composition for preventing or treating a cancer.

BEST MODE FOR CARRYING OUT THE INVENTION

Figure 1:
FIG. 1 shows HCRs of the CD99 protein.

Throughout the specification, the term "inflammation" or "inflammatory diseases" include acute and/or chronic inflammatory diseases, e.g., rheumatoid arthritis, adhesive capsulitis, sinovitis, coxarthritis, osteoarthritis, osteoporosis, periarthritis, multiple sclerosis, osteomyelitis, systemic lupus erythematosus, polymyalgia rheumatic (PMR), Sjogren's Syndrome, progressive systemic sclerosis (scleroderma), ankylosing spondylitis, polymyositis, dermatomyositis, pemphigus, pemphigoid, Type I diabetes mellitus, myasthenia gravis, Hashimoto's thyroditis, Graves' disease, Goodpasture's disease, mixed connective tissue disease, sclerosing cholangitis, inflammatory bowel disease (including Crohn's Disease and ulcerative colitis), inflammatory dermatoses, inflammatory respiratory diseases (including usual interstitial pneumonitis (UIP), lymphoid interstitial pneumonia, giant cell interstitial pneumonia, cellular interstitial pneumonia, desquamative interstitial pneumonia, asbestosis, silicosis, berylliosis, talcosis, pneumoconiosis, Adult Respiratory Distress Syndrome, and extrinsic allergic alveolitis), immediate hypersensitivity reactions (including asthma and hayfever), sarcoidosis, Wegener's granulomatosis, various angiitis, chronic active hepatitis, delayed-type hypersensitivity reactions (including poison ivy dermatitis), cutaneous allergies, psoriatic arthritis, Reiter's syndrome, immediate hypersensitivity reactions, rheumatic fever, acute or chronic glomerulonephritis, acute exacerbations, pyelonephritis, cellulitis, cystitis, acute cholecystitis, inflammatory aortic aneurysm, atherosclerosis, Still's disease, Parkinson's disease, Alzheimer's disease. The polypeptide or its fusion protein of the present invention can be also administered to patients suffering from diseases involving inflammatory diseases, e.g., reperfusion injuries, autoimmune diseases, organ transplantation rejection or tissue allograft organ rejection, etc. Thus, the "inflammation" or "inflammatory diseases" as used herein are meant to comprehend diseases involving inflammatory diseases. The polypeptide or its fusion protein of the present invention can be used preferably in rheumatoid arthritis, osteoporosis, respiratory inflammation, autoimmune diseases, and/or organ transplantation rejection; more preferably in rheumatoid arthritis, autoimmune diseases, and/or organ transplantation rejection; particularly preferably, in acute contact dermatitis, allergic inflammation, or rheumatoid arthritis.

It is newly found by the present invention that the ligands of various lengths derived from highly conserved regions (HCRs) of CD99 and its family, i.e., CD99 (SEQ ID NO: 1), CD99L2(SEQ ID NO: 2), and PBDX(or XG) (SEQ ID NO: 3) can inactivate $\beta_1$ integrin through binding to CD99 molecules. Furthermore, it is newly found by the present invention that the polypeptide including a certain sequence derived from HCRs of CD99 and its family can inhibit angiogenesis and transmigration of cancer cells through inactivating the $\beta_1$ integrin of endothelial cells and cancer cells, thereby providing anticancer activity.

Especially, it is also newly found that, according to sequence analysis of the polypeptides, the sequence of Leu-Xaa-Asp is a minimum unit for inactivating the $\beta_1$ integrin. The Xaa may be any amino acid, preferably Ser, Gly, Ala, or Glu, which are respectively the peptides of SEQ ID NOs: 11 to 14. Therefore, it is found by the present invention that the proteins derived from CD99, CD99L2, or PBDX(or XG) comprising the sequence of Leu-Xaa-Asp can show anti-inflammatory activity by blocking the transmigration of leukocytes through inactivation of $\beta_1$ integrin; and can show anticancer activity by inhibiting angiogenesis of endothelial cells and transmigration of cancer cells through inactivation of $\beta_1$ integrin. Preferably, the protein or its fusion protein may be applied to solid cancers such as breast cancer, gastric cancer, colorectal cancer, colon cancer, rectal cancer, and pancreatic cancer; or lymphoma.

The present invention provides a polypeptide having an inhibitory activity against transmigration of leukocytes or an inhibitory activity against growth and/or metastasis of cancer cells, wherein the polypeptide is selected from the group consisting of a polypeptide consisting of 3 to 96 amino acids derived from the polypeptide of SEQ ID NO: 1, said polypeptide comprising the peptide from position 28 to position 30 or from position 55 to position 57 of SEQ ID NO: 1, with the proviso that a polypeptide comprising the peptide from position 94 to position 97 of SEQ ID NO: 1 is excluded; a polypeptide consisting of 3 to 200 amino acids derived from the polypeptide of SEQ ID NO: 2, said polypeptide comprising the peptide from position 32 to position 34, from position 73 to position 75, from position 121 to position 123, or from position 150 to position 152 of SEQ ID NO: 2; and a polypeptide consisting of 3 to 130 amino acids derived from the polypeptide of SEQ ID NO: 3, said polypeptide comprising the peptide from position 27 to position 29 of SEQ ID NO: 3. Preferably, the polypeptide of the present invention may be selected from the group consisting of polypeptides as set forth in SEQ ID NOs: 4 to 14.

The present invention also includes, within its scope, a fusion protein of the polypeptide and a polyhistidine (poly-His) region or a fusion protein of the polypeptide and a Fc region. The poly-His region, which is a tag peptide, can be used for the separation and purification of the polypeptide of the present invention by binding to a histidine binding resin. In the fusion protein of the present invention, the poly-His region may have the amino acid sequence as set forth in SEQ ID NO: 15. The Fc region can be used for increasing stability in the blood of the polypeptide. In the fusion protein of the present invention, the Fc region may have the amino acid sequence as set forth in SEQ ID NO: 16.

The present invention also includes, within its scope, a polynucleotide encoding the polypeptide. The polynucleotide can be prepared from the nucleic acid sequences encoding CD99, CD99L2, or PBDX(or XG), using a known method in the art. The polynucleotide may have the nucleotide sequence as set forth in SEQ ID NOs: 20 to 33.

The present invention also includes, within its scope, a vector comprising the polynucleotide encoding the polypeptide. Various known cloning vectors, e.g., pPICZα A, B, or C (Invitrogen, U.S.A.), may be used as a cloning vector. Preferably, a vector including DNA encoding a poly-His region (e.g., SEQ ID NO: 34), for example, a pET28a(+) vector (Novagen, U.S.A.) may be used as a cloning vector. And also, a vector obtained by inserting DNA encoding a Fc region (e.g., cDNA consisting of the nucleotide sequence as set forth in SEQ ID NO: 35) into a conventional vector, e.g., a pET28a (+) vector (Novagen, U.S.A.) may be used as a cloning vector. The vector of the present invention can be constructed by inserting the polynucleotide encoding the polypeptide into a cloning vector with an appropriate restriction enzyme site using a method commonly known in the art. The vector of the present invention may be directly used in a gene therapeutic composition for the purpose of gene therapy or may be used in the production of transformants.

The present invention also includes, within its scope, a transformant obtained by transforming a host cell with the vector. The host cell is not particularly limited as long as the polypeptide can be effectively expressed. Preferably, the host cell may be selected from microorganisms belonging to the genus Escherichia (e.g., Escherichia coli), the genus Pichia (e.g., X-33 Pichia; Invitrogen, U.S.A.), etc.

The present invention also provides a pharmaceutical composition for the prevention or treatment of inflammatory diseases, comprising the polypeptide or fusion protein as an active ingredient and a pharmaceutically acceptable carrier.

The present invention also provides a pharmaceutical composition for inhibiting the growth and/or metastasis of cancer cells, comprising the polypeptide or its fusion protein as an active ingredient and a pharmaceutically acceptable carrier.

The pharmaceutical compositions of the present invention may include excipients such as lactose or corn starch, lubricants such as magnesium stearate, currently available emulsifiers, suspending agents, buffers, isotonic agents, etc. The pharmaceutical compositions of the present invention can be administered orally or parenterally. Preferably, the pharmaceutical compositions of the present invention can be formulated into parenteral dosage forms. For intramuscular, intraperitoneal, subcutaneous, or intravenous administration, a sterilized solution of an active ingredient is generally prepared. In this case, the sterilized solution may include a buffer to achieve a desired pH value. With respect to formulations for intravenous administration, an isotonic agent may be used to render the formulations isotonic. The pharmaceutical compositions of the present invention can be formulated into aqueous solutions including a pharmaceutically acceptable carrier such as a saline of pH 7.4. The aqueous solutions can be introduced into a patient's intramuscular blood stream by local bolus injection.

The pharmaceutical composition of the present invention can be administered to patients who suffer from various inflammatory diseases, solid cancer (such as breast cancer, gastric cancer, colorectal cancer, colon cancer, rectal cancer, pancreatic cancer) or lymphoma at a daily dosage of about 1 to 2000 mg/kg. An adequate dosage is generally changed according to age, body weight, and conditions of a patient.

Hereinafter, the present invention will be described more specifically by the following working examples. However, the following working examples are provided only for illustrations and thus the present invention is not limited to or by them.

Example 1

Synthesis of Polypeptides cDNA fragments of SEQ ID NOs: 20 and 21 encoding respective polypeptides of SEQ ID NOs: 4 and 5 were inserted into pET28a(+)-Fc vectors (prepared by inserting cDNAs of SEQ ID NO: 35, which encodes the Fc regions of human immunoglobulin, into pET28a(+) vectors) to produce pET28a-CD99L2EXT-Fc vectors and pET28a-PBDX(or XG)EXT-Fc vectors. That is, the cDNA fragments of SEQ ID NOs: 20 and 21 were isolated by PCR, digested with EcoRI, and inserted into the EcoRI sites of pET28a(+)-Fc vectors with ligation enzymes to produce the pET28a-CD99L2EXT-Fc vectors and pET28a-PBDX(or XG)EXT-Fc vectors.

Colonies obtained by transforming BL21(DE3) cells with the obtained expression vectors were cultured in LB media for about 4 to 6 hours. When the absorbance (A600) of the cultures reached 0.4-0.6, protein expression was induced by isopropyl β-D-1-thiogalactopyranoside (IPTG) (1.4 mM) for 7 to 9 hours. The cells were precipitated by centrifugation, washed with phosphate buffered saline (PBS), and then re-precipitated to remove impurities from the media. Fractions were analyzed by SDS-PAGE gel to check protein expression.

For purification of expressed proteins, an 8M urea buffer (8M urea, 0.01M Tris-Cl, 0.1M $NaH_2PO_4$) was used. The pH of the urea buffer was adjusted to 8.0, 6.3, 4.5, etc. according to a purification step. The cells were lysed with a pH 8.0 urea buffer containing protease inhibitors (1 mM PMSF, 10 μg/Ml leupeptin, 1 μg/Ml pepstatin, 1 μg/Ml aprotinin) and centrifuged at 13,000 rpm for 20 minutes at 4° C. The supernatants were mixed with histidine (His)-binding resins (N-NTA His Bind Resins, Novagen, U.S.A.) in a 1 Ml Eppendorf tube, and the mixtures were incubated at 4° C. for 16 hours to induce the binding of histidine residues of the expressed proteins and the His-binding resins. The reaction solutions were centrifuged, the supernants were discarded, and the pellets were washed with a pH 6.3 urea buffer. The protein was then dialyzed against PBS, and stored in aliquots in a cold store.

The peptides of SEQ ID NOs: 6 to 14 were synthesized with an automatic peptide synthesizer (PeptrEx-R48, Peptron, Daejeon, Korea) using a FMOC solid-phase method. The synthesized peptides were purified and analyzed by reverse-phase high-performance liquid chromatography (reverse-phase HPLC) (Prominence LC-20AB, Shimadzu, Japan) using a C18 analytical RP column (Shiseido capcell pak), and isolated using a mass spectrometer (HP 1100 Series LC/MSD, Hewlett-Packard, Roseville, U.S.A.).

TABLE 1

| Protein Name | Fragments | Polypeptide | cDNA |
|---|---|---|---|
| CD99FL | 1~185 | SEQ ID NO: 1 | SEQ ID NO: 17 |
| CD99L2FL | 1~262 | SEQ ID NO: 2 | SEQ ID NO: 18 |
| PBDX(or XG)FL | 1~180 | SEQ ID NO: 3 | SEQ ID NO: 19 |
| CD99L2EXT | 26~184 | SEQ ID NO: 4 | SEQ ID NO: 20 |
| PBDX(or XG)EXT | 18~136 | SEQ ID NO: 5 | SEQ ID NO: 21 |
| CD99HCRI-7 | 26~32 | SEQ ID NO: 6 | SEQ ID NO: 22 |
| CD99HCRII-7 | 53~59 | SEQ ID NO: 7 | SEQ ID NO: 23 |
| CD99L2HCRI-7 | 30~36 | SEQ ID NO: 8 | SEQ ID NO: 24 |
| CD99L2HCRII-7 | 119~125 | SEQ ID NO: 9 | SEQ ID NO: 25 |
| PBDX(orXG)HCRII-7 | 25~31 | | SEQ ID NO: 26 |
| CD99L2HCRIII-8 | 145~152 | SEQ ID NO: 10 | SEQ ID NO: 27 |
| CD99HCRI-3 | 28~30 | SEQ ID NO: 11 | SEQ ID NO: 28 |
| CD99HCRII-3 | 55~57 | SEQ ID NO: 12 | SEQ ID NO: 29 |
| CD99L2HCRII-3 | 121~123 | SEQ ID NO: 13 | SEQ ID NO: 30 |
| PBDX(or XG)HCRII-3 | 27~29 | | SEQ ID NO: 31 |
| CD99L2HCRI-3 | 32~34 | SEQ ID NO: 14 | SEQ ID NO: 32 |
| CD99L2HCRIII-3 | 150~152 | | SEQ ID NO: 33 |

FL: full length
EXT: external domain
HCR: highly conserved region

Example 2

Preparation of Polypeptide-Containing Compositions

The polypeptides of SEQ ID NOs: 4 to 14 were dissolved in PBS to a concentration of 3 µg/100 µl. The resultant protein solutions were also used in the following experimental examples.

Experimental Example 1

Tests for Inactivation of $\beta_1$ Integrin Expressed in Human Monocytes (U937)

Effects of the peptide fragments of SEQ ID NOs: 6 to 14 on inactivation of $\beta_1$ integrin expressed in human monocytes (U937) were tested.

U937 cells ($5 \times 10^4$) were added to each well and then treated with the protein solutions including each peptide of SEQ ID NOs: 6 to 14 in PBS (5~30 µg/Ml) prepared as in Example 2. After incubation for 1 hour, the cells were washed with PBS three times and then subject to lysis in 1% NP40 lysis buffer (1% Nonidet P40, 0.1M NaCl, 0.05M tris (pH 8.0), 5 mM EDTA) supplemented with 0.1 µM PMSP (phenylmethylsulfonyl fluoride), 1 µg/Ml pepstatin A, 10 µg/Ml leupeptin, 1 µg/Ml aprotinin, and 1 mM $Na_3VO_4$.

The cell lysates were subject to electrophoresis on 10% polyacrylamide gel. For identifying an activated $\beta_1$ integrin, the electrophoresis was performed under non-reducing condition, i.e., without β-mercaptoethanol. The separated proteins were transferred to a nitrocellulose membrane, and then treated with a blocking solution (Tris-buffered saline (TBS) containing 0.05% Tween 20 and 3% bovine serum albumin) at room temperature for about 1 hour. The proteins were incubated for 2 hours, in a TBS buffer supplemented with anti-$\beta_1$ integrin monoclonal antibodies (Chemicon Co.; cat. No. MAB2259Z) specific to the activated form of $\beta_1$ integrin. After washing with a TBS buffer containing 0.05% Tween 20, the proteins were treated with horseradish peroxidase conjugated anti-mouse IgG (DiNonA Co.; cat. No. 80019F) at room temperature for 1 hour. After washing five times with a TBS buffer containing 0.05% Tween 20, the proteins were visualized using an antibody detection kit (iNtRON Biotechnology, Inc). For confirming the experiment on the same amount of cell lysate, actin was also detected using anti-beta actin monoclonal antibodies (Sigma-Aldrich Ltd.; cat No. A54441). The results are shown in FIGS. 2 to 4.

Figure 2:
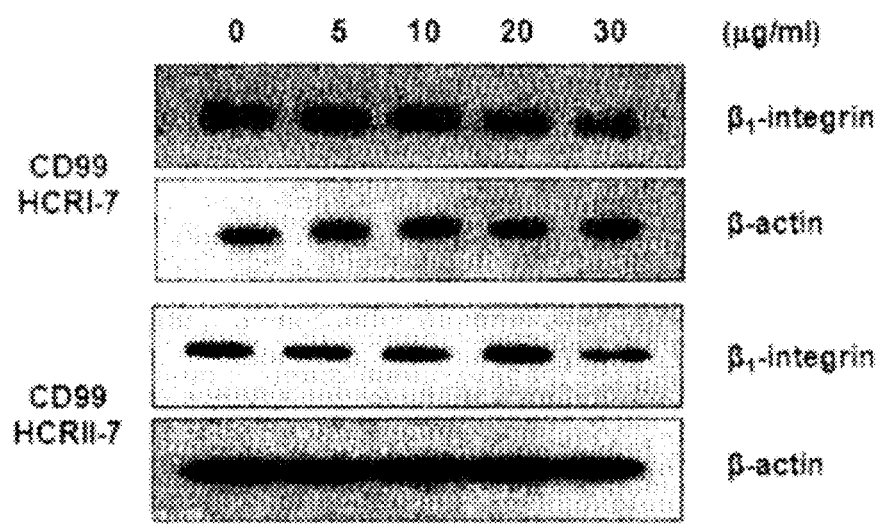
FIGS. 2 to 4 are the results obtained by evaluating the effects of the polypeptides of the present invention on inactivation of $\beta_1$ integrin.
Figure 3:
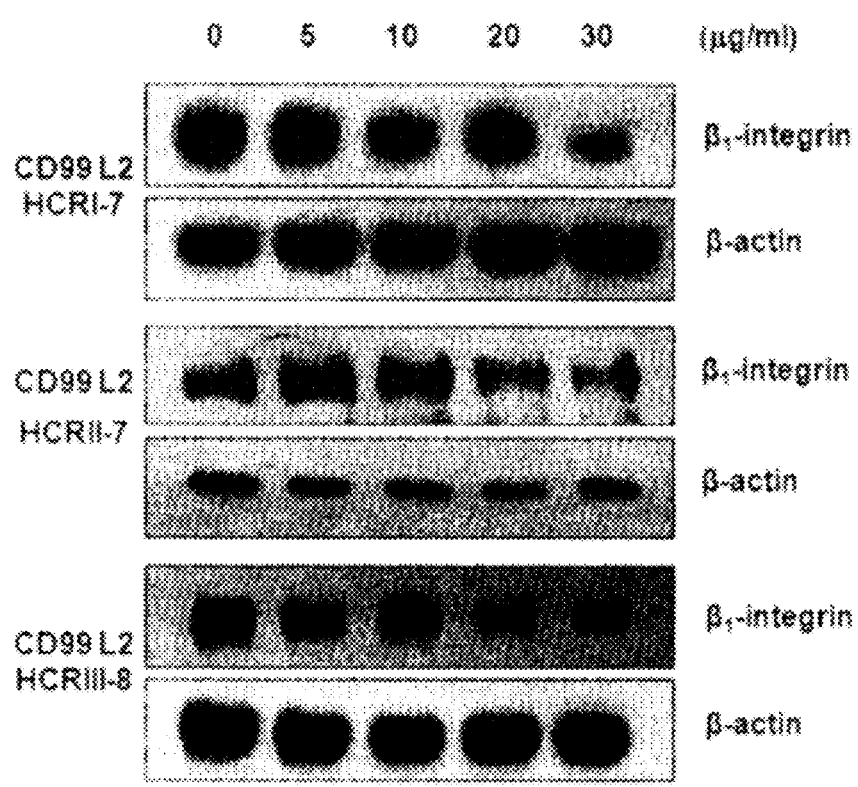
Figure 4:
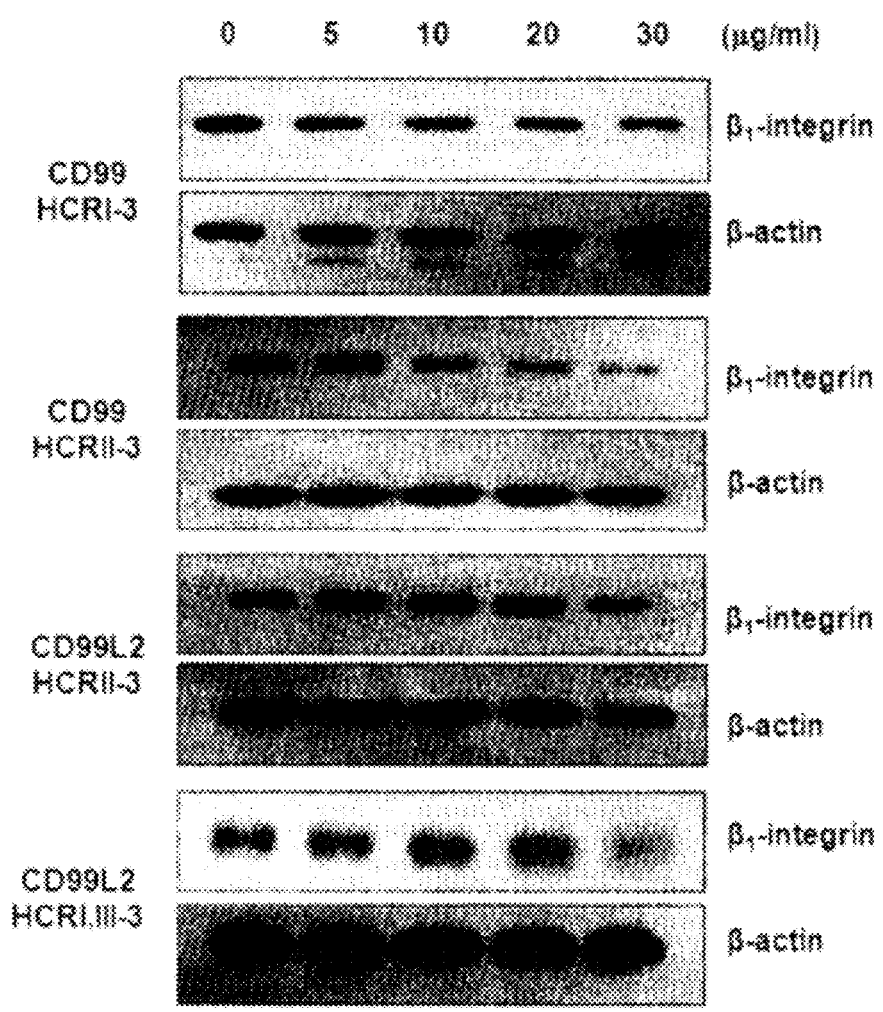

In FIGS. 2 to 4, QKKKLCF or LCF derived from the internal domain of CD99 was used as a control peptide. Referring to FIGS. 2 to 4, in the groups treated with the polypeptides of the present invention, $\beta_1$ integrin was inactivated in dose-dependent manner. However, when treated with the polypeptide not including the amino acids of SEQ ID NOs: 11 to 14, such a reduction was not observed (data not shown).

Experimental Example 2

Figure 5:
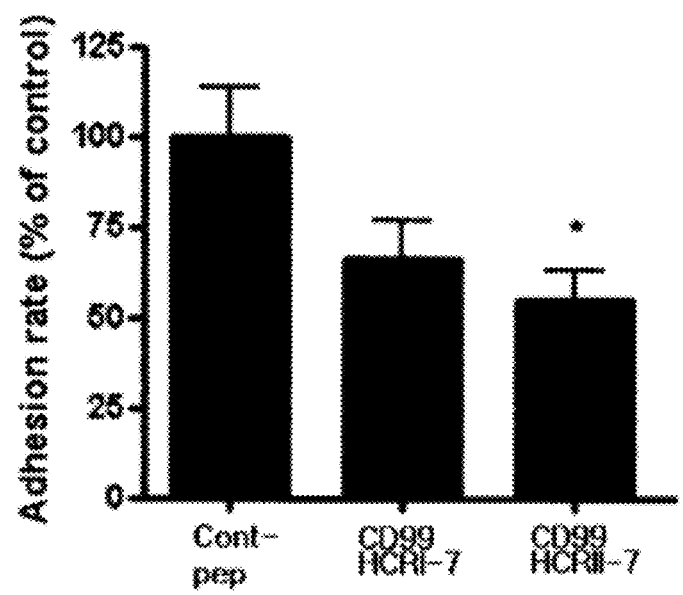
FIGS. 5 to 7 are the results obtained by evaluating the effects of the polypeptides of the present invention on adhesion between human monocytes (U937) and human umbilical vein endothelial cells.
Figure 6:
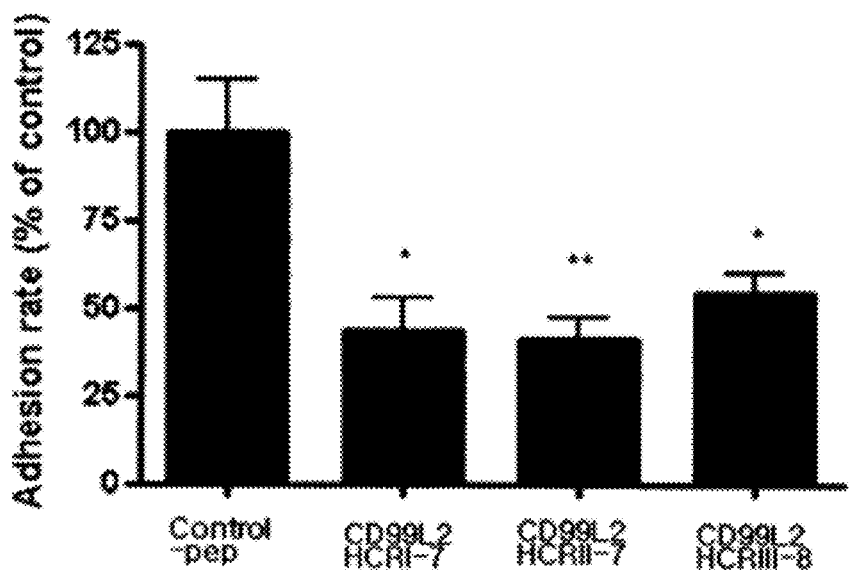
Figure 7:
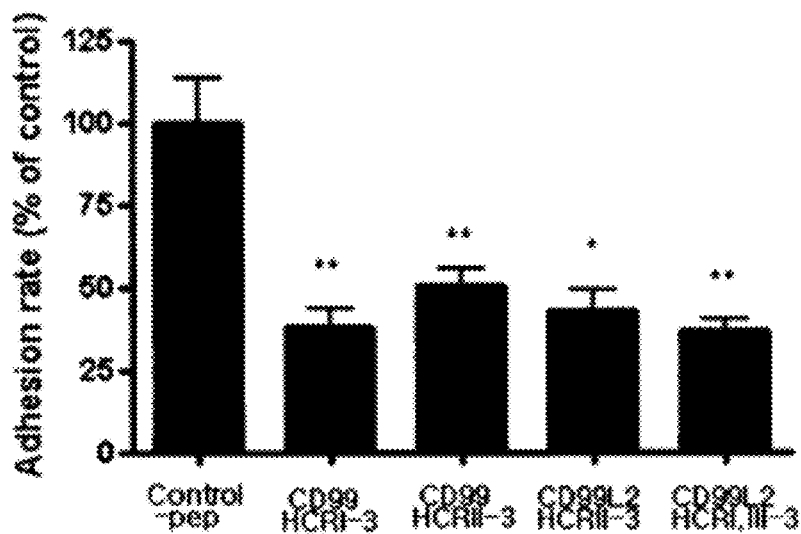

Tests for Inhibitory Activity Against Adhesion Between Human Monocytes (U937) and HUVECs Effects of the peptide fragments of SEQ ID NOs: 6 to 14 on adhesion between human monocytes (U937) and human umbilical vein endothelial cells (HUVECs) were tested. HUVECs ($5 \times 10^4$) were added to each well of a 96-well culture plate. After incubation in 5% $CO_2$ at 37° C. for 24 hours, HUVECs were activated by treating with IL-1β for 4 hours, and then each well was washed with serum-free media. U937 cells ($1 \times 10^5$) were treated for 1 hour with the protein solutions including each peptides of SEQ ID NOs: 6 to 14 in PBS (5~30 µg/Ml) prepared as in Example 2. The resulting U937 cells were washed with serum-free media three times and then added to each well containing the HUVECs. After incubation for 1 hour at 37° C., the cells were washed one time with PBS and then detached from the extracellular matrix using trypsin-EDTA. The number of the U937 cells having small and circular shape unlike HUVECs was determined under an inverted microscope, using a hemacytometer. The results are shown in FIGS. 5 to 7. In FIGS. 5 to 7, QKKKLCF or LCF was used as a control peptide.

Referring to FIGS. 5 to 7, in the groups treated with the polypeptides of the present invention, the number of monocytes adhered to HUVECs was reduced by about 30~60% relative to the control group. And also, in case treated with the fusion proteins, i.e., pET28a-hCD99L2-Fc and pET28a-PBDX-Fc, similar results were obtained (data not shown). However, in the group treated with the polypeptide not including the amino acids of SEQ ID NOs: 11 to 14, such a reduction was not observed. Thus, it is expected that the polypeptide including the amino acids of SEQ ID NOs: 11 to 14 can inhibit trans-endothelial migrations of the monocytes.

Experimental Example 3

Figure 8:
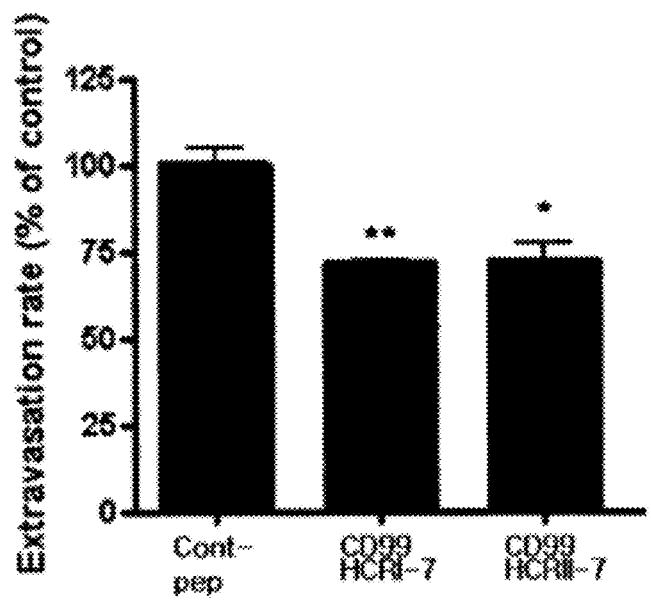
FIGS. 8 to 10 are the results of trans-endothelial migration assays for human monocytes (U937), after treating with the polypeptides of the present invention.
Figure 9:
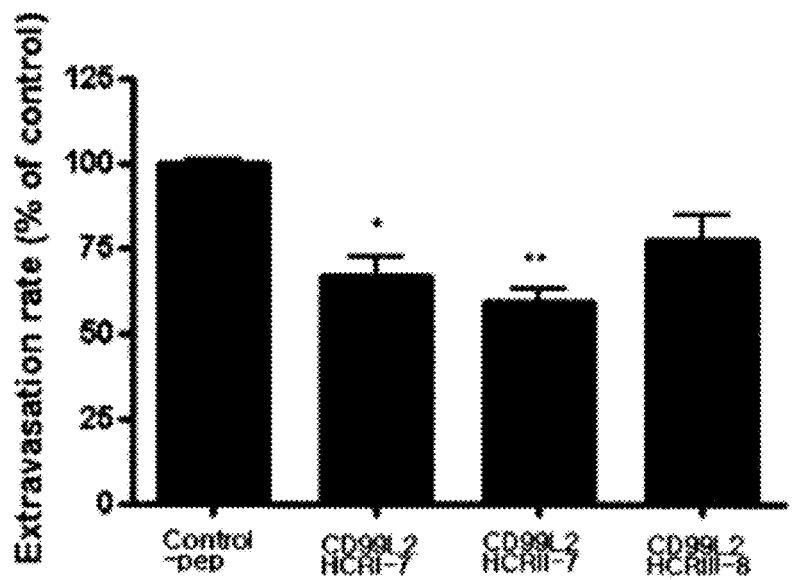
Figure 10:
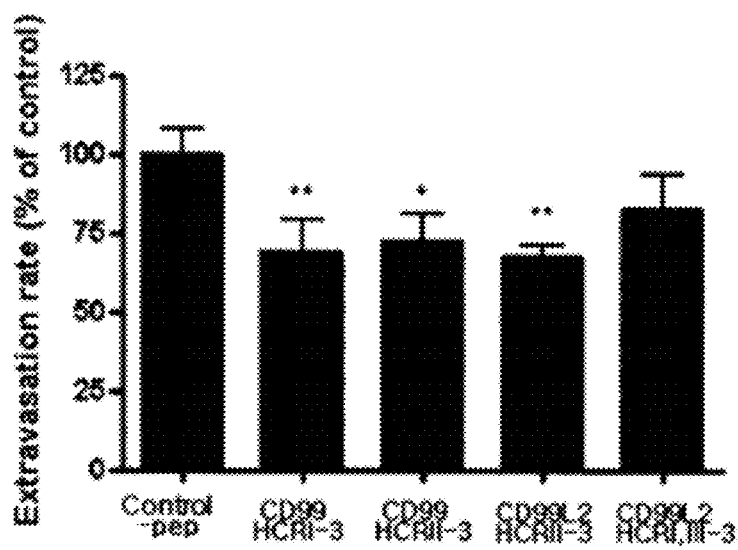

Tests for Inhibitory Activity Against In Vitro Trans-Endothelial Migration of Monocytes HUVECs were cultured in the upper compartments of Boyden chambers. The supernatants were removed, and human monocytes (U937), which had been untreated or treated for 1 hour with the protein solutions including each peptide of SEQ ID NOs: 6 to 14 in PBS (30 NM) prepared as in Example 2, were seeded at $5 \times 10^5$ cells/chamber. At this time, a culture including a supernatant obtained by centrifugation of a culture obtained after culturing NIH/3T3 mouse fibroblasts in serum-free DMEM containing 0.005% vitamin C and 0.1% bovine serum albumin for 16 hours was placed in the lower compartments of the chambers to induce the invasion of the monocytes. The chambers were incubated for 6 hours, and the number of the cells migrated to the lower compartments was measured. The test was repeated five times, and the results are shown in FIGS. 8 to 10. The control peptide is a peptide consisting of QKKKLCF or LCF.

Referring to FIGS. 8 to 10, trans-endothelial migrations of the monocytes in the groups treated with the polypeptides of the present invention were significantly reduced (about 25~40% reduction) as compared with that in the control group. Taking into consideration that trans-endothelial migration is essential for migration of leukocytes into inflammation sites through blood vessels, it is expected that the polypeptides according to the present invention can effectively inhibit the inflammatory reaction.

Experimental Example 4

Tests for Inhibitory Activity Against Acute Contact Dermatitis

Anti-inflammatory activities of the polypeptides according to the present invention were investigated. 250 uM PMA (phorbol 12-myristate 13-acetate) was applied to one ear of BALB/c mice (about 6 weeks old) so as to induce acute contact dermatitis. At the same time, the protein solutions (100 µl) prepared by dissolving each peptide fragment of SEQ ID NOs: 11 to 14 (100 µg) in PBS (100 µl) was injected through the tail vain of the dermatitis-induced mice. A solution (100 µl) prepared by dissolving the control peptide (i.e., QKKKLCF) (100 µg) in PBS (100 µl) was also injected in the same manner. After 6 hours, induction and severeness of dermatitis was evaluated by measuring the ear weights. The measurement of ear weights was performed by collecting the same size of ear-samples from the three sites of each ear with a punch and then weighing the obtained samples.

Figure 11:
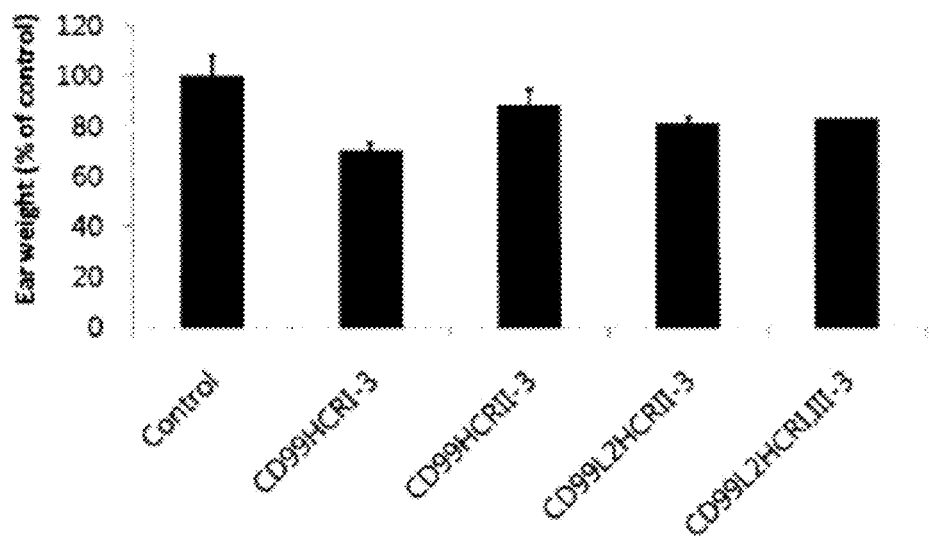
FIG. 11 shows the comparative values of ear weights, after injecting the polypeptides of the present invention into acute contact dermatitis-induced mice.

FIG. 11 is the graph obtained by comparing the ear weights of the test group mice (treated with the polypeptides of the present invention) with those of the control group mice (not treated with the peptide). Referring to FIG. 11, in the groups treated with the polypeptides according to the present invention, the ear weighs were reduced by about 15-30% relative to the control group. Thus, it is expected that the polypeptide of the present invention, including the peptides of SEQ ID NOs: 11 to 14, can effectively inhibit the inflammatory reaction.

Experimental Example 5

Tests for Inhibitory Activity Against IgE-Mediated Immediate Hypersensitivity Reactions Anti-allergic activity of the polypeptide according to the present invention was investigated. Balb/c mice (about 6 weeks old) were sensitized by injecting IgE antibody (5 µg) through the tail vain thereof. After 24 hours, the protein solution (100 µl) prepared by dissolving the peptide fragment of SEQ ID NO: 13 (100 µg) in PBS (100 µl) was injected through the tail vain of the sensitized mice. A 0.15% DNFB solution [2,4-d]nitrofluorobenzene in aceton: olive oil (4:1)] as an antigen was applied on each ear of the mice so as to induce IgE-mediated immediate hypersensitivity. In case of the negative control mice, only PBS (100 µl) was injected without treating a 0.15% DNFB solution. In case of the positive control mice, PBS (100 µl) was injected and then a 0.15% DNFB solution was treated. The changes in ear thickness were measured with a digital caliper every hour for 12 hours. Every day from the third day, the peptide fragment of SEQ ID NO: 13 (100 µg) was intraperitoneally injected to the test group mice, while only PBS was intraperitoneally injected to the control group mice. The changes in ear thickness were measured for 15 days.

Figure 12:
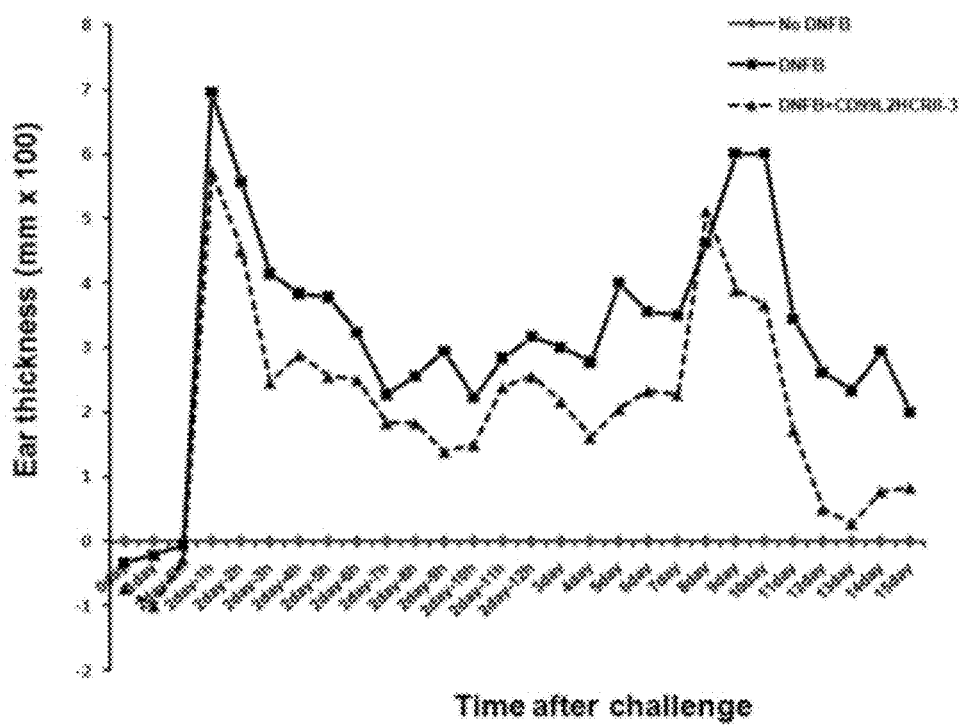
FIG. 12 is the results obtained by measuring the ear thickness changes, after injecting the polypeptides of the present invention into IgE-mediated immediate hypersensitivity reaction-induced mice.

FIG. 12 is the graph obtained by comparing the ear thickness changes of the test group mice and the positive control mice (increased by treating a 0.15% DNFB solution) with those of the negative control. Referring to FIG. 12, in the groups injected with the polypeptide according to the present invention, the ear thickness increments were remarkably decreased relative to the positive control group. Thus, it is expected that the polypeptides according to the present invention, including the peptide of SEQ ID NO: 13, can effectively inhibit an IgE-mediated immediate hypersensitivity reaction.

Experimental Example 6

Tests for Inhibitory Activity Against Collagen-Induced Arthritis (CIA)

Inhibitory activity of the peptide according to the present invention against rheumatoid arthritis was investigated. A mixture (50 µl) having an equal volume (1:1) of CFA (Complete Freund's Adjuvant) and Bovine type II collagen (2 mg/Ml) was injected subcutaneously in the tail base of C57BL/6 mice (male, 4 weeks old). After 2 weeks, a mixture having an equal volume (1:1) of Bovine type II collagen (2 mg/Ml) and Incomplete Freund's Adjuvant was additionally injected into the sole of the foot. When the mean arthritis score reached 9-12 by the induction of CIA, mice were randomly divided into a test group and a control group. The test group was orally administered with a solution of the peptide fragment of SEQ ID NO: 13 (100 µg) in PBS (100 µl), while the control group was orally administered with only PBS (100 µl). And then, the mean arthritis scores were measured with naked eyes and statistically analyzed for 21 days. The mean arthritis score was assigned, based on the following criteria: 0=normal, 1=edema in less than 1 toe, 2=edema in more than 2 toes, 3=edema in the sole & edema in edema in less than 1 toe, 4=edema in the sole of the foot & edema in more than 2 toes or edema in the sole of the foot and the ankle & edema in less than 1 toe, 5=stiffness of tow.

Figure 13:
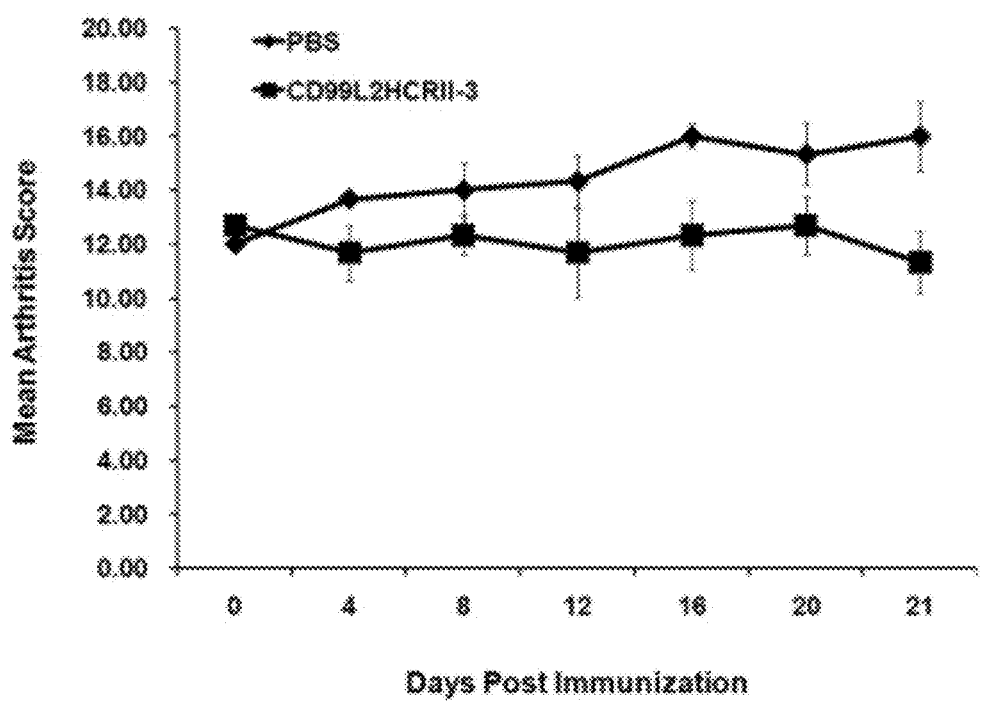
FIG. 13 shows the results obtained by measuring the mean arthritis scores, after administering the polypeptides of the present invention to the mice having collagen-induced arthritis (CIA).

FIG. 13 shows the results obtained by measuring the mean arthritis scores of the control group (treated with only PBS) and the test group (treated with the peptide according to the present invention). Referring to FIG. 13, in the test groups orally administered with the peptide according to the present invention, the arthritis was significantly inhibited.

Experimental Example 7

Tests for Inhibitory Activity Against Adhesion of HUVECs to Extracellular Matrix Effects of the polypeptides of SEQ ID NOs: 4 to 14 on adhesion of human umbilical vein endothelial cells (HUVECs) to fibronectin were tested.

Figure 14:
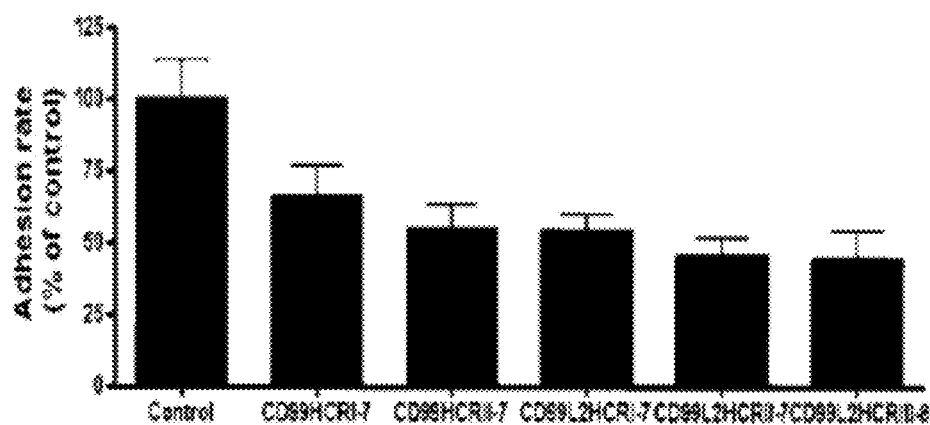
FIGS. 14 to 16 are the results obtained by evaluating the effects of the polypeptides of the present invention on adhesion of human umbilical vein endothelial cell (HUVEC) to fibronectin
Figure 15:
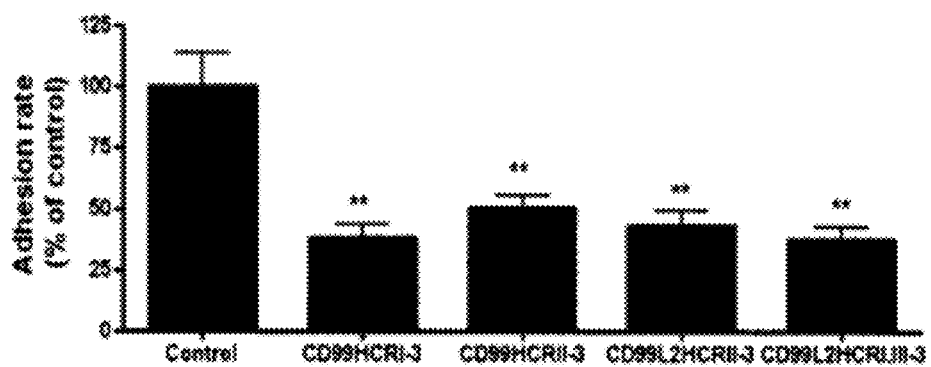
Figure 16:
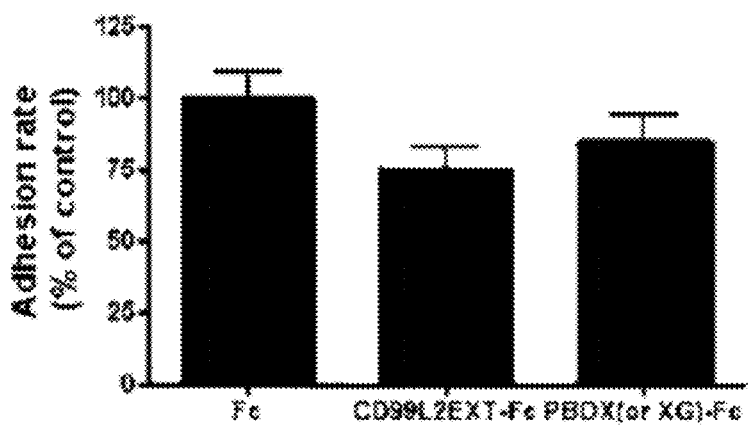

Each well of a 96-well culture plate was coated with fibronectin, a component of extracellular matrix, and then dried under UV light. HUVECs ($5 \times 10^4$) were dispensed into each well, and then the protein solutions including each peptide of SEQ ID NOs: 4 to 14 prepared as in Example 2 were treated to each well, in the concentration of 3 µg/ml. After incubation for 1 hour, the cells were washed three times with PBS, detached using trypsin-EDTA, and then stained with a trypan-blue solution. The number of the cells adhered to fibronectin was determined using a hemacytometer. The results are shown in FIGS. 14 to 16. In FIGS. 14 to 16, QKKKLCF or LCF derived from the internal domain of CD99 was used as a control peptide.

Referring to FIGS. 14 to 16, in the test groups treated with the polypeptides of the present invention, the number of HUVECs adhered to fibronectin was reduced by about 30-60% relative to the control group. And also, in case treated with the fusion proteins, i.e., CD99L2EXT-Fc and PBDX(or XG)-Fc, similar results were obtained (FIG. 16). In this case, the control protein was a human IgG Fc, i.e., the protein as set forth in SEQ ID NO: 16.

Experimental Example 8

Tests for Inhibitory Activity Against In Vitro Angiogenesis

Effects of the polypeptides of the present invention on angiogenesis were evaluated.

Figure 17:
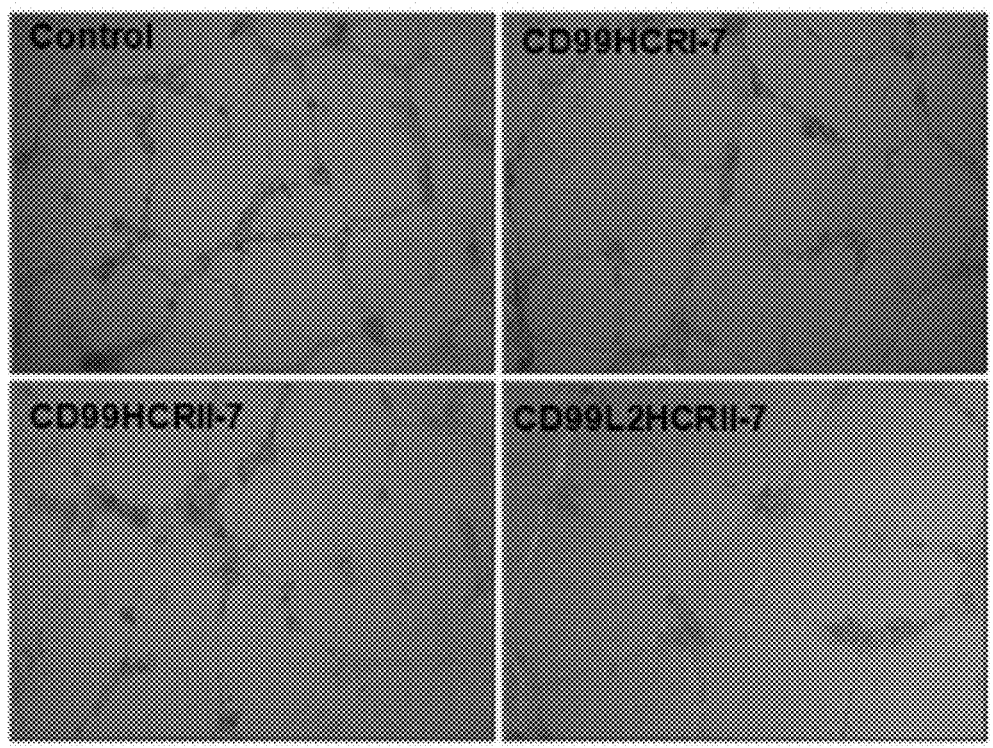
FIGS. 17 to 19 are the results obtained by evaluating the effects of the polypeptides of the present invention on angiogenesis of human umbilical vein endothelial cell (HUVEC).
Figure 18:
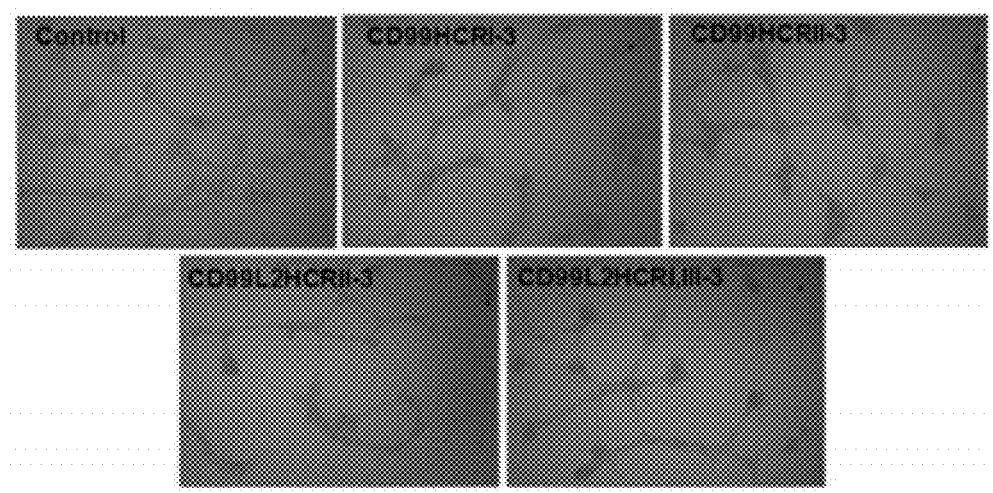
Figure 19:
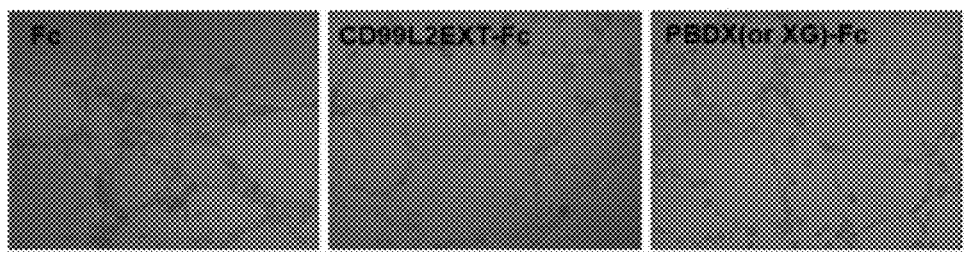

Generally, interactions of basement membrane components of blood vessels with vascular endothelial cells play an important role in formation and maintenance of new blood vessels. When Matrigel, basement membrane components, is treated to 24-well culture plate, plugs are formed through polymerization reaction. HUVECs were seeded at a density of $8 \times 10^4$ cells/well to each well of 24-well culture plates coated with Matrigel. The protein solutions including each peptide of SEQ ID NOs: 4 to 14 (30 μg/Ml) prepared as in Example 2 and bFGF (basic fibroblast growth factor, 150 μg/Ml) were added to the wells. After incubation for 24 hours, formation of new blood vessels was examined using an inverted microscope (at 50× magnification), and the results are shown in FIGS. 17 to 19. The control peptide and protein are the same peptide and Fc as used in Experimental Example 1 and 7.

Referring to FIGS. 17 to 19, when HUVECs were treated with the protein solution including the polypeptide of the present invention, tube formation (i.e., angiogenesis) was significantly reduced. And also, in case treated with the fusion proteins, i.e., CD99L2EXT-Fc and PBDX(or XG)-Fc, similar results were obtained (FIG. 19).

Experimental Example 9

Tests for Inhibitory Activity Against Invasion of Cancer Cells

Each well of a transwell was coated with fibronectin, which is a ligand of integrin. MCF-7 human breast cancer cells ($5 \times 10^5$ cells) were loaded to the upper compartment of the transwell and then incubated for 24 hours. When about 80% of the cells were grown up, each well was treated with the protein solutions including each peptide of SEQ ID NOs: 4 to 14 in PBS (30 μg/Ml) prepared as in Example 2. After incubation in 5% CO2 at 37° C. for 1 hour, each well was treated with 0.1% BSA. Invasion-inducing medium (the supernatant obtained by incubating NIH/3T3 cells in the serum-free DMEM supplemented with 0.005% of vitamin C and 1% of BSA for 24 hours) was loaded into the lower compartment. Cells migrated into the lower compartments of the transwell were counted three times at 24-hour intervals, and then the results were statistically analyzed. The control peptide and protein are the same peptide and Fc as used in Experimental Example 1 and 7. The results are shown in FIGS. 20 to 22.

Figure 20:
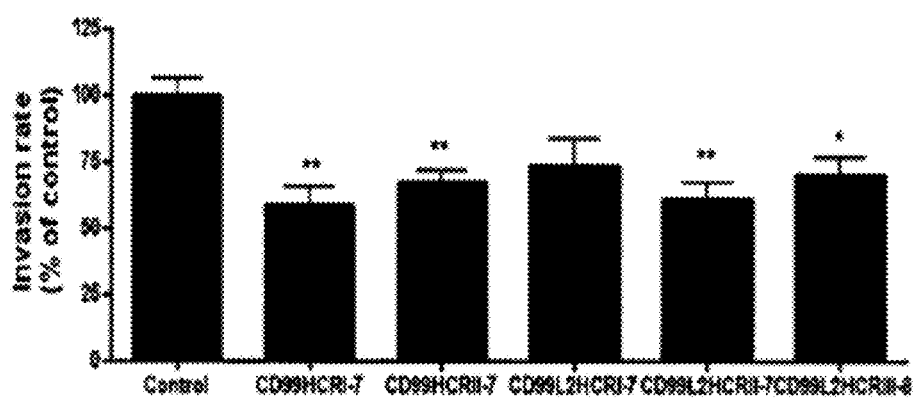
FIGS. 20 to 22 are the results of invasion assay for human breast carcinoma cells (MCF-7), after treating with the polypeptides of the present invention.
Figure 21:
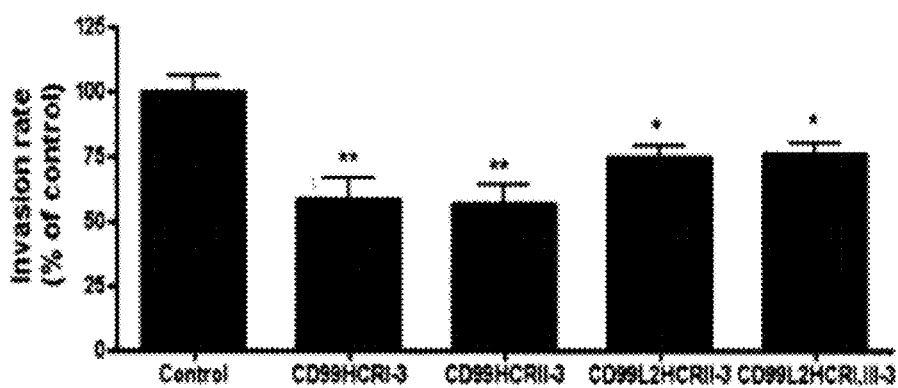
Figure 22:
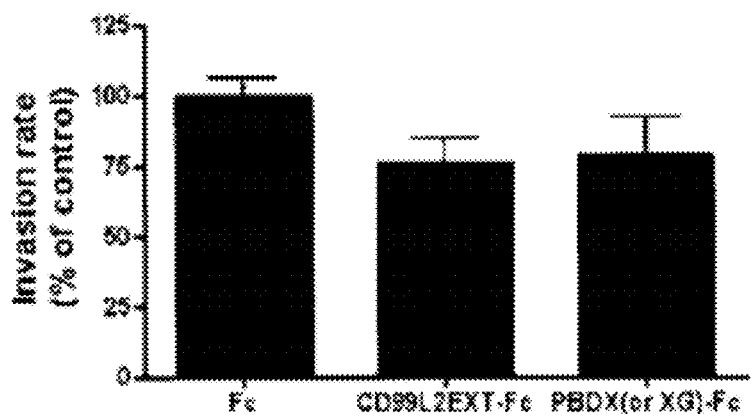

Referring to FIGS. 20 to 22, in the groups treated with the peptides of SEQ ID NOs: 4 to 14 according to the present invention, the invasion rate of the human breast cancer cells was reduced by about 60% relative to that of the control group treated with the control peptide. Taking into consideration that cancer cells come out from blood vessels and invade basement membranes or surrounding connective tissues and then spread to secondary sites, it can be seen that polypeptides of the present invention can effectively inhibit the metastasis of cancer cells.

Experimental Example 10

Figure 23:
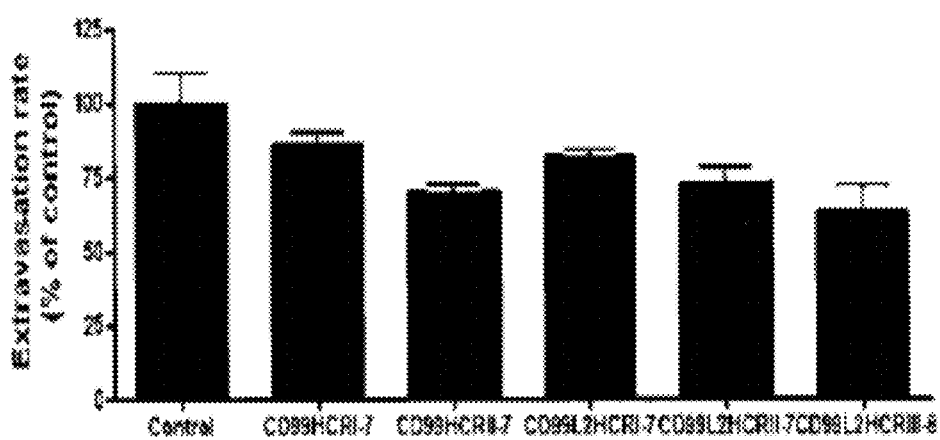
FIGS. 23 to 25 are the results of trans-endothelial migration assays for human breast carcinoma cells (MCF-7), after treating with the polypeptides of the present invention.
Figure 24:
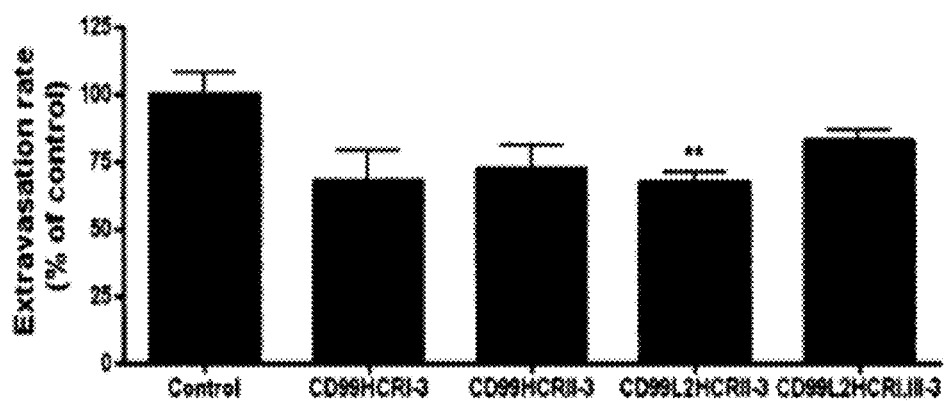
Figure 25:
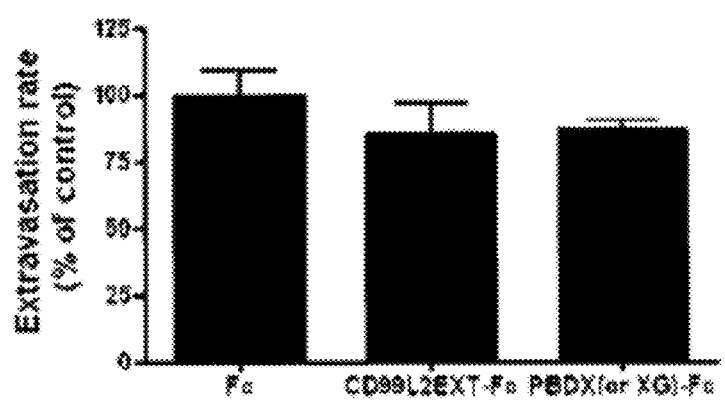

Tests for Inhibitory Activity Against In Vitro Trans-Endothelial Migration of Cancer Cells HUVECs were cultured in the upper compartments of Boyden chambers. The supernatants were removed, and MCF-7 human breast cancer cells, which had been untreated or treated for 1 hour with the protein solutions including each peptide of SEQ ID NOs: 4 to 14 in PBS (30 μg/Ml) prepared as in Example 2, were seeded at $5 \times 10^5$ cells/chamber. At this time, the invasion-inducing medium was loaded into the lower compartments of the chambers to induce the invasion of the breast cancer cells. The chambers were incubated for 6 hours, and the number of the cells migrated to the lower compartments was measured. The test was repeated more than three times, and the results are shown in FIGS. 23 to 25. In FIGS. 23 to 25, the control peptide and protein are the same peptide and Fc as used in Experimental Example 1 and 7.

Referring to FIGS. 23 to 25, trans-endothelial migrations of the breast cancer cells in the groups treated with the polypeptides of the present invention were reduced to about 60 to 80% of that in the control group. Taking into consideration that trans-endothelial migration is essential for migration of cancer cells into organs through blood vessels, it can be seen that polypeptides of the present invention can effectively inhibit the metastasis of cancer cells.

The invention claimed is:

1. An isolated polypeptide selected from the group consisting of the polypeptides as set forth in SEQ ID NOs: 4-10, 12 and 13.

2. A fusion protein wherein a polyhistidine (poly-His) region is fused to the polypeptide of claim 1.

3. The fusion protein of claim 2, wherein the poly-His region has the amino acid sequence as set forth in SEQ ID NO: 15.

4. A fusion protein wherein a Fc region is fused to the polypeptide of claim 1.

5. The fusion protein of claim 4, wherein the Fc region has the amino acid sequence as set forth in SEQ ID NO: 16.

6. A pharmaceutical composition for the treatment of inflammatory diseases, comprising the polypeptide of claim 1 as an active ingredient and a pharmaceutically acceptable carrier.

7. The pharmaceutical composition of claim 6, wherein the inflammatory disease is acute contact dermatitis, allergic inflammation, or rheumatoid arthritis.

8. A pharmaceutical composition for inhibiting the metastasis of cancer cells or angiogenesis, comprising the polypeptide of claim 1 as an active ingredient and a pharmaceutically acceptable carrier.

9. The pharmaceutical composition of claim 8, wherein the cancer cells is breast cancer cells, gastric cancer cells, colorectal cancer, colon cancer cells, rectal cancer cells, pancreatic cancer cells, or lymphoma cells.

10. A pharmaceutical composition for the treatment of inflammatory diseases comprising the fusion protein of claim 2 as an active ingredient and a pharmaceutically acceptable carrier.

11. A pharmaceutical composition for inhibiting the metastasis of cancer cells or angiogenesis, comprising the fusion protein of claim 2 as an active ingredient and a pharmaceutically acceptable carrier.

12. A method of treatment of inflammatory diseases comprising administering to a subject in need thereof a therapeutically effective amount of the pharmaceutical composition of claim 6 or of a pharmaceutical composition comprising an isolated peptide that consists of the amino acid sequences as set forth in SEQ ID NOs: 11 or 14 and a pharmaceutically acceptable carrier.

13. The method of claim 12 wherein the inflammatory disease is acute contact dermatitis, allergic inflammation, or rheumatoid arthritis.

14. A method of inhibiting the metastasis of breast cancer cells or angiogenesis comprising administering to a subject in need thereof a therapeutically effective amount of the pharmaceutical composition of claim 6 or of a pharmaceutical composition comprising an isolated peptide that consists of the amino acid sequences as set forth in SEQ ID NOs: 11 or 14 and a pharmaceutically acceptable carrier.

* * * * *